United States Patent
Wang et al.

(10) Patent No.: US 8,811,700 B2
(45) Date of Patent: Aug. 19, 2014

(54) EXACT LOCAL COMPUTED TOMOGRAPHY BASED ON COMPRESSIVE SAMPLING

(75) Inventors: Ge Wang, Blacksburg, VA (US); Hengyong Yu, Winston-Salem, NC (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 142 days.

(21) Appl. No.: 13/264,834

(22) PCT Filed: Apr. 15, 2010

(86) PCT No.: PCT/US2010/031262
§ 371 (c)(1),
(2), (4) Date: Nov. 30, 2011

(87) PCT Pub. No.: WO2010/121043
PCT Pub. Date: Oct. 21, 2010

(65) Prior Publication Data
US 2012/0063659 A1    Mar. 15, 2012

Related U.S. Application Data

(60) Provisional application No. 61/169,577, filed on Apr. 15, 2009.

(51) Int. Cl.
*G06K 9/00*           (2006.01)
(52) U.S. Cl.
USPC ........................................................ 382/128
(58) Field of Classification Search
None
See application file for complete search history.

(56) References Cited

U.S. PATENT DOCUMENTS

| | | | | |
|---|---|---|---|---|
| 7,424,088 B2 * | 9/2008 | Zamyatin et al. | ................. | 378/4 |
| 7,697,658 B2 * | 4/2010 | Wang et al. | ....................... | 378/4 |
| 8,014,616 B2 * | 9/2011 | Chakraborty et al. | ........ | 382/233 |
| 2005/0135664 A1 | 6/2005 | Kaufhold et al. | | |
| 2007/0110290 A1 | 5/2007 | Chang et al. | | |

OTHER PUBLICATIONS

Guang-Hong Chen, Jie Tang, and Shuai Leng; "Prior image constrained compressed sensing (PICCS): A method to accurately reconstruct dynamic CT images form highly undersampled projection data set", 28, Jan. 2008; Medical Physics Letter.*
Jose L. Paredes, Gonzalo R Arce, Zhongmin Wang; "Ultra-Wideband Compressed Sensing: Channel Estimation" Oct. 2007, IEEE Journal of Selected Topics in Signal Processing.*
Hengyong Yu, Guohau Cao, Laurel Burk, Yueh Lee, Jianping Lu, Pete Santago, Otto Zhou, Ge Wang; "Compressive Sampling Based Interior Reconstruction for Dynamic Carbon Nanotube Micro-CT"; Jan. 2009, NIH Public Access.*
Lu Gan; "Block Compressed Sensing of Natural Images"; 2007, IEEE.*
D. Donoho. "Compressed Sensing" Stanford University, 2004, hereinafter Donoho.*

(Continued)

*Primary Examiner* — Barry Drennan
*Assistant Examiner* — Oneal R Mistry
(74) *Attorney, Agent, or Firm* — Blank Rome LLP

(57) ABSTRACT

A system and method for tomographic image reconstruction using truncated projection data that allows exact interior reconstruction (interior tomography) of a region of interest (ROI) based on the known sparsity models of the ROI, thereby improving image quality while reducing radiation dosage. In addition, the method includes parallel interior tomography using multiple sources beamed at multiple angles through an ROI and that enables higher temporal resolution.

50 Claims, 5 Drawing Sheets

(56) References Cited

OTHER PUBLICATIONS

Candes et al (Non-Patent Literature: "Fast Discrete Curvelets Transforms," Department of Statistics, Stanford University, Stanford, CA, 2005.*
Chen et al (Non-Patent Literature: "Prior Image Constrained Compressed sensing (PICCS): A method to Accurately reconstruct dynamic CT images from highly undersampled projection data sets," NIH Public Access, Med. Phys. 2008, 35(2): 660-663. 2008.*
D. Donoho. "Compressed Sensing" Stanford University, 2004.*
Paredes et al (Non-Patent Literature: "Ultra-Wideband Compressed Sensing: Channel Estimation", IEEE, vol. 1 No. 3, 10. 2007.*
Yu et al., "SART-type image reconstruction from a limited number of projections with the sparsity constraint", Hindawi Publishing Corp., International Journal of Biomedical Imaging, vol. 2010, Article ID 934847, 9 pages, Received Dec. 31, 2009; Accepted Feb. 10, 2010.
Yang, et al., "High-order total variation minimization for interior tomography", 2010 IOP Publishing Ltd., Recv'd Aug. 15, 2009, published: Feb. 25, 2010.
Yu, et. al, "Interior SPECT-exact and stable ROI reconstruction from uniformly attenuated local projects", Commun. Numer. Meth. Engng 2009; 25:693-710: Published Jan. 5, 2009.
Daubechies, et al., "Accelerated Projected Gradient Method for Linear Inverse Problems with Sparsity Constraints", J. Fourier Anal. Appl. (2008); 14:764-792
Yu, et al., "Compressive sampling based interior reconstruction for dynamic carbon nanotube micro-CT", Journal of X-Ray Science & Tech, 17 (2009) 295-303.
Daubechies, et al., "An iterative thresholding algorithm for linear inverse problems with a sparsity constraint", Feb. 1, 2008.
Courdurier, et al., "Solving the interior problem of computed tomography using a priori knoweldge", IOP Publishing, (2008).
Candes, et al., "Robust Uncertainty Principles: Exact Signal Reconstruction from Highly Incomplete Frequency Information", IEEE Transactions on Information Theory, vol. 52, No. 2, Feb. 2006.
Donoho, "Compressed Sensing", IEEE Transactions on Information Theory. vol. 52, No. 4, Apr. 2006.
Yu, et al., "Compressed sensing based interior tomography", IOP Publishing, Phys. Med. Biol. 54 (2009) 2791-2805.
Defrise, et al., "Truncated Hilbert transform and image reconstruction from limited tomographic data", Institute of Physics Publishing, (2006) 1037-1053.
Xu, et al., "Statistical Interior Tomography", IEEE Transactions on Medical Imaging, vol. 30, No. 5, May 2011.
Yu, et al., "A soft-threshold filtering approach for reconstruction from a limited number of projections", IOP Publishing, Pys. Med. Biol. 55 (2010) 3905-3916.
Chen, et al., "Temporal resolution improvement using PICCS in MDCT cardiac imaging", Med. Phys. 36 (6), Jun. 2009, 2130-2135.
Han, et al., "A General Total Variation Minimization Theorem for Compressed Sensing Based Interior Tomography", Hindawi Publishing Corp., Internat'l J. of Biomed. Imaging, vol. 2009, Article ID 125871, 3 pgs.
Wang, et al., "Ordered-subset simultaneous algebraic; reconstruction techniques (OS-SART)", Journal of X-Ray Science & Tech. 12 (2004) 169-177, IOP Press.
Yu, et al., "Interior reconstruction using the truncated Hilbert transform via singular value decomposition", Journal of X-Ray Science and Tech., 16 (2008) 243-251.
Kudo, "Tiny a priori knoweldge solves the interior problem in computed tomography", IOP Publishing, Phys. Med. Biol., 53 (2008) 2207-2231.
Noo, et al., "A two-step Hilbert transform method for 2D image reconstruction", 2004 IOP Pub. Ltd., Phys. Med. Biol. 49 (2004) 3903-3923.
Yu, et al., "Supplemental analysis on compressed sensing based interior tomography", IOP Publishing, Phys. Med. Biol. 54 (2009) N425-N432.
Chen, et al., "Prior image constrained compressed sensing (PICCS): A method to accurately reconstruct dynamic CT images from highly undersampled projection data sets", Med. Phys. 35 (2), Feb. 2008.
Sidky, et al., "Accurate image reconstruction from few-views and limited-angle data in divergent-beam CT", IOS Press, Journal of X-Ray Science and Technology 14 (2006) 119-139.
Ye, et al., "Exact Interior Reconstruction from Truncated Limited-Angle Projection Data", Hindawi Publ. Corp., Internat'l Journal of Biomed. Imaging, vol. 2008, Article ID 427989, 6 pgs.
Ye, et al., "A General Local Reconstruction Approach Based on a Truncated Hilbert Transform", Hindawi Publ. Corp., Internat'l Journal of Biomed. Imaging, vol. 2007, Article ID 63634, 8 pgs.
Yu, "SART-Type Image Reconstruction from Overlapped Projections", Hindawi Pub. Corp., Internat'l Journal of Biomed. Imaging, vol. 2011, Article ID 549537, 7 pgs.
Yang, "Compressed Sensing Inspired Image Reconstruction from Overlapped Projections", Hindawi Publ. Corp., Internat'l Journal of Biomed. Imaging, vol. 2010, Article ID 284073, 8 pgs.
Ye, et al., "Exact Interior Reconstruction with Cone-Beam CT", Hindawi Publ. Corp., Internat'l Journal of Biomed. Imaging, vol. 2007, Article ID 10693, 5 pgs.

* cited by examiner

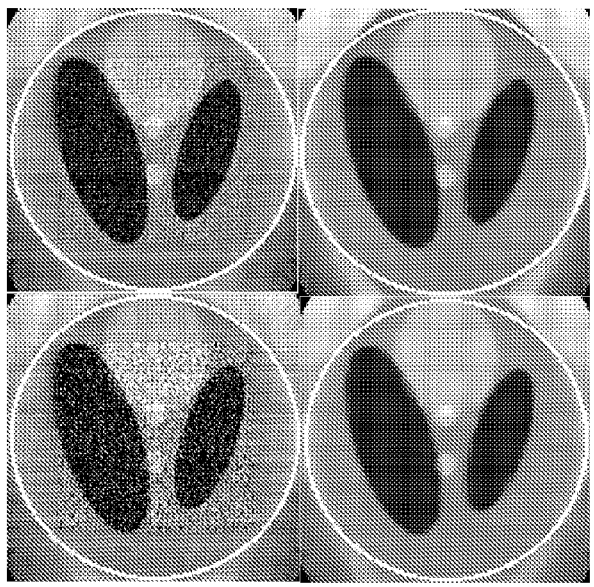 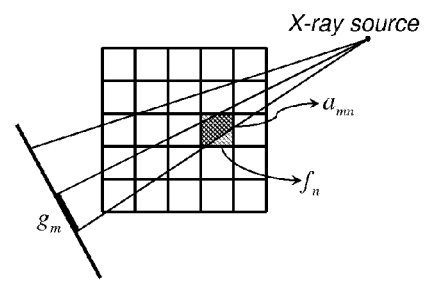
Figure 7.
Figure 8.
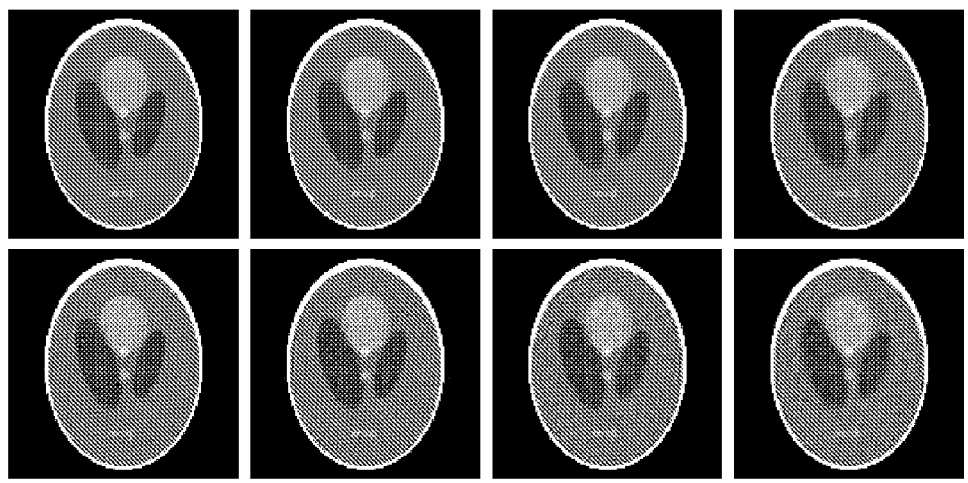
Figure 9.

(A) (B) (C) (D)

(A) (B) (C)

EXACT LOCAL COMPUTED TOMOGRAPHY BASED ON COMPRESSIVE SAMPLING

STATEMENT OF GOVERNMENT INTEREST

This invention was made with government support under Grant Nos. EB002667, EB004287 and EB007288 awarded by National Institutes of Health. The Government has certain rights in the invention.

CROSS-REFERENCE TO RELATED APPLICATIONS

This application claims priority to U.S. Provisional Application Ser. No. 61/169,577, filed Apr. 15, 2009. The complete content of that application is herein incorporated by reference.

BACKGROUND OF THE INVENTION

1. Field of the Invention

The present invention relates to x-ray computed tomography (CT) and, more particularly, to systems and methods for theoretically exact interior reconstruction using compressive sampling (or compressed sensing or under another name for the essentially same thing) technology that is based an appropriate signal sparsity model, with the extension of such techniques to other tomographic modalities, such as PET/SPECT, MRI, and others that use imaging geometries of straight rays or nearly straight rays.

2. Background Description

One conventional wisdom is that the interior problem (exact reconstruction of an interior ROI only from data associated with lines through the ROI) does not have a unique solution (see F. Natterer, *The mathematics of computerized tomography*. Classics in applied mathematics 2001, Philadelphia: Society for Industrial and Applied Mathematics). Nevertheless, it is highly desirable to perform interior reconstruction for radiation dose reduction and other important reasons. Hence, over past years a number of image reconstruction algorithms were developed that use an increasingly less amount of raw data (D. L. Parker, *Optimal short scan convolution reconstruction for fanbeam ct*. Med. Phys., 1982. 9(2): p. 254-257; F. Noo, R. Clackdoyle, and J. D. Pack, *A two-step hilbert transform method for 2d image reconstruction*. Physics in Medicine and Biology, 2004. 49(17): p. 3903-3923; M. Defrise, et al., *Truncated hilbert transform and image reconstruction from limited tomographic data*. Inverse Problems, 2006. 22(3): p. 1037-1053). Specifically, motivated by the major needs in cardiac CT, CT guided procedures, nano-CT and so on (G. Wang, Y. B Ye, and H. Y Yu, Interior tomography and instant tomography by reconstruction from truncated limited-angle projection data, U.S. Pat. No. 7,697,658, Apr. 13, 2010), by analytic continuation we proved that the interior problem can be exactly and stably solved if a sub-region in an ROI within a field-of-view (FOV) is known (see Y. B. Ye, et al., *A general local reconstruction approach based on a truncated hilbert transform*. International Journal of Biomedical Imaging, 2007, Article ID: 63634, 8 pages; Y. B. Ye, H. Y. Yu, and G. Wang, *Exact interior reconstruction with cone-beam CT*. International Journal of Biomedical Imaging, 2007, Article ID: 10693, 5 pages; Y. B. Ye, H. Y. Yu, and G. Wang, *Exact interior reconstruction from truncated limited-angle projection data*. International Journal of Biomedical Imaging, 2008 ID: 427989, 6 Pages; H. Y. Yu, Y. B. Ye, and G. Wang, *Local reconstruction using the truncated hilbert transform via singular value decomposition*. Journal of X-Ray Science and Technology, 2008. 16(4): p. 243-251). Similar results were also independently reported by others (see H. Kudo, et al., *Tiny a priori knowledge solves the interior problem in computed tomography*. Phys. Med. Biol., 2008. 53(9): p. 2207-2231; M. Courdurier, et al., *Solving the interior problem of computed tomography using a priori knowledge*. Inverse Problems, 2008, Article ID 065001, 27 pages.). Although the CT numbers of certain sub-regions such as air in a trachea and blood in an aorta can be indeed assumed, how to obtain precise knowledge of a sub-region generally can be difficult in some cases such as in studies on rare fossils or certain biomedical structures. Therefore, it would be very valuable to develop more powerful interior tomography techniques.

Another conventional wisdom is that data acquisition should be based on the Nyquist sampling theory, which states that to reconstruct a band-limited signal or image, the sampling rate must at least double the highest frequency of non-zero magnitude. Very interestingly, an alternative theory of compressive sampling (or compressed sensing or under another name for the essentially same thing) (CS) has recently emerged which shows that high-quality signals and images can be reconstructed from far fewer data/measurements than what is usually considered necessary according to the Nyquist sampling theory (see D. L. Donoho, *Compressed sensing*. IEEE Transactions on Information Theory, 2006. 52(4): p. 1289-1306; E. J. Candes, J. Romberg, and T. Tao, *Robust uncertainty principles: Exact signal reconstruction from highly incomplete frequency information*. IEEE Transactions on Information Theory, 2006. 52(2): p. 489-509). The main idea of CS is that most signals are sparse in an appropriate domain (an orthonormal system or more generally a frame system), that is, a majority of their coefficients are close or equal to zero, when represented in that domain. Typically, CS starts with taking a limited amount of samples in a much less correlated basis, and the signal is exactly recovered with an overwhelming probability from the limited data via the L1 norm minimization (or minimization of another appropriate norm). Since samples are limited, the task of recovering the image would involve solving an underdetermined matrix equation, that is, there is a huge amount of candidate images that can all fit the limited measurements effectively. Thus, some additional constraint is needed to select the "best" candidate. While the classical solution to such problems is to minimize the L2 norm, the recent CS results showed that finding the candidate with the minimum L1 norm, also basically equivalent to the total variation (TV) minimization in some cases (L. L. Rudin, S. Osher, and E. Fatemi, *Nonlinear total variation based noise removal algorithms*. Physica D, 1992. 60(1-4): p. 259-268), is a reasonable choice, and can be expressed as a linear program and solved efficiently using existing methods (see D. L. Donoho, *Compressed sensing*. IEEE Transactions on Information Theory, 2006. 52(4): p. 1289-1306; E. J. Candes, J. Romberg, and T. Tao, *Robust uncertainty principles: Exact signal reconstruction from highly incomplete frequency information*. IEEE Transactions on Information Theory, 2006. 52(2): p. 489-509).

Because the x-ray attenuation coefficient often varies mildly within an anatomical component, and large changes are usually confined around borders of tissue structures, the discrete gradient transform (DGT) has been widely utilized as a sparsifying operator in CS-inspired CT reconstruction (for example, E. Y. Sidky, C. M. Kao, and X. H. Pan, *Accurate image reconstruction from few-views and limited-angle data in divergent-beam ct*. Journal of X-Ray Science and Technology, 2006. 14(2): p. 119-139; G. H. Chen, J. Tang, and S. Leng, *Prior image constrained compressed sensing (piccs): A* method to accurately reconstruct dynamic ct images from highly undersampled projection data sets. Medical Physics, 2008. 35(2): p. 660-663; H. Y. Yu, and G. Wang, *Compressed sensing based interior tomography*. Phys Med Biol, 2009. 54(9): p. 2791-2805; J. Tang, B. E. Nett, and G. H. Chen, *Performance comparison between total variation (tv)-based compressed sensing and statistical iterative reconstruction algorithms*. Physics in Medicine and Biology, 2009. 54(19): p. 5781-5804). This kind of algorithms can be divided into two major steps. In the first step, an iteration formula (e.g. SART) is used to update a reconstructed image for data discrepancy reduction. In the second step, a search method (e.g. the standard steepest descent technique) is used in an iterative framework for TV minimization. These two steps need to be iteratively performed in an alternating manner. However, there are no standard stopping and parameter selection criteria for the second step. Usually, these practical issues are addressed in an ad hoc fashion.

On the other hand, soft-threshold nonlinear filtering (see M. A. T. Figueiredo, and R. D. Nowak, *An em algorithm for wavelet-based image restoration*. IEEE Transactions on Image Processing, 2003. 12(8): p. 906-916; I. M. Daubechies, M. Defrise, and C. De Mol, *An iterative thresholding algorithm for linear inverse problems with a sparsity constraint*. Communications on Pure and Applied Mathematics, 2004. 57(11): p. 1413-1457; I. M. Daubechies, M. Fornasier, and I. Loris, *Accelerated projected gradient method for linear inverse problems with sparsity constraints*. Journal of Fourier Analysis and Applications, 2008. 14(5-6): p. 764-792) was proved to be a convergent and efficient algorithm for the norm minimization regularized by a sparsity constraint. Unfortunately, because the DGT is not invertible, it does not satisfy the restricted isometry property (RIP) required by the CS theory (see D. L. Donoho, *Compressed sensing*. IEEE Transactions on Information Theory, 2006. 52(4): p. 1289-1306; E. J. Candes, J. Romberg, and T. Tao, *Robust uncertainty principles: Exact signal reconstruction from highly incomplete frequency information*. IEEE Transactions on Information Theory, 2006. 52(2): p. 489-509) and soft-threshold algorithm (see I. M. Daubechies, M. Defrise, and C. De Mol, *An iterative thresholding algorithm for linear inverse problems with a sparsity constraint*. Communications on Pure and Applied Mathematics, 2004. 57(11): p. 1413-1457; I. M. Daubechies, M. Fornasier, and I. Loris, *Accelerated projected gradient method for linear inverse problems with sparsity constraints*. Journal of Fourier Analysis and Applications, 2008. 14(5-6): p. 764-792). In other words, the soft-threshold algorithm cannot be directly applied for TV minimization. The above problem can be overcome using an invertible sparsifying transform such as a wavelet transform for image compression. For an object of interest such as a medical image, we can find an orthonormal basis (or more generally, a frame) to make the object sparse in terms of significant transform coefficients. Then, we can perform image reconstruction from a limited number of non-truncated or truncated projections by minimizing the corresponding L1 norm.

Inspired by the CS theory, we proved and demonstrated the interior tomography is feasible in the CS framework assuming a sparsity model; specifically a piecewise-constant image model and a number of high-order models (see H. Y. Yu, and G. Wang, *Compressed sensing based interior tomography*. Phys Med Biol, 2009. 54(9): p. 2791-2805; H. Y. Yu, et al., *Supplemental analysis on compressed sensing based interior tomography*. Phys Med Biol, 2009. 54(18): p. N425-N432; W. M. Han, H. Y. Yu and G. Wang; *A general total variation minimization theorem for compressed sensing based interior tomography*; International Journal of Biomedical Imaging, Article ID: 125871, 2009, 3 pages; H. Y. Yu, et al; *Compressive sampling based interior tomography for dynamic carbon nanotube Micro-CT*; Journal of X-ray Science and Technology, 17(4): 295-303, 2009). The above finding has been extended to interior SPECT reconstruction assuming a piecewise-polynominial image model and introducing a high-order total variation concept (H. Y. Yu, J. S. Yang, M. Jiang, G. Wang: *Methods for Exact and Approximate SPECT/PET Interior Reconstruction*. VTIP No.: 08-120, U.S. Patent Application No. 61/257,443, Date Filed: Nov. 2, 2009), CT is a special case of SPECT when the attenuation background is negligible (J. S. Yang, H. Y. Yu, M. Jiang and G. Wang; *High order total variation minimization for interior tomography*, Inverse Problems, 26(3), Article ID: 035013, 2010, 29 pages). Based on the recent mathematical findings made by Daubechies et al., we adapted a simultaneous algebraic reconstruction technique (SART) for image reconstruction from a limited number of projections subject to a sparsity constraint in terms of an invertible sparsifying transform (H. Y. Yu and G. Wang: *SART-type image reconstruction from a limited number of projections with the sparsity constraint*; International Journal of Biomedical Imaging, Article ID: 934847, 2010, to appear), and constructed two pseudo-inverse transforms of un-invertible transforms for the soft-threshold filtering (H. Y. Yu and G. Wang: *Soft-threshold filtering approach for reconstruction from a limited number of projections*, Physics in Medicine and Biology, pending revision).

SUMMARY OF THE INVENTION

An exemplary object is to provide a new method and system for providing interior tomography with sparsity constraints from truncated local projections, which may or may not be aided by other data and/or knowledge.

Another exemplary object is to provide instant tomography where a ROI or VOI is imaged without moving an X-ray source on a path around a patient/animal/specimen/object. For purposes of this description the ROI will be understood to include VOI, and vice versa.

According to one exemplary embodiment, the interior problem can be solved in a theoretically exact and numerically reliable fashion if the ROI is subject to an appropriate sparsity image model. The reconstruction schemes only use projection data associated with lines through an ROI or volume of interest (VOI) to be reconstructed, and are referred to as interior tomography, in contrast with traditional CT reconstruction that does not allow two-side data truncation. Interior tomography enables faithful resolution of features inside an ROI using data collected along x-ray beams probing the ROI with knowledge of the sparsity model (e.g., piecewise constant, high-order, and wavelet transform). The reconstruction is to minimize the L1 norm of the ROI image in the sparsifying transform domain. The sparsifying transform can be invertible transforms or frames, such as a wavelet transform, Fourier transform, and other lossless digital image compressive transforms. And the sparsity transform can also be un-invertible transform, such as the discrete gradient transform or discrete difference transform. The L1 norm minimization can be, for example, implemented by the steepest decent method, soft-threshold filtering method and its accelerated projected gradient version, as well as pseudo-inverse transforms of the discrete gradient transform and discrete difference transform.

According to another exemplary embodiment, novel fan-beam or cone-beam techniques are developed which permit higher temporal resolution at less radiation dose. That is, CT systems and methods can use interior tomography to provide ultrafast or instantaneous temporal resolution of a small ROI with or without the need to move an x-ray source on a trajectory around a patient/animal/object, producing a "snapshot", herein referred to as ultrafast or instant tomography. In addition, the user can move to another region of interest or "roam" to re-position or enlarge such a snapshot, shifting the CT imaging paradigm. This reduced time for imaging will enrich image information with improved temporal resolution, and, for example, result in increased numbers of screening procedures that can be performed on an individual scanning apparatus providing additional benefits of reduced requirements for data storage and cost savings. In this type of systems, using some sparsity models CS-based interior reconstruction is performed to offer excellent imaging performance.

BRIEF DESCRIPTION OF THE DRAWINGS

The foregoing and other objectives, aspects and advantages will be better understood from the following detailed description of a preferred embodiment of the invention with reference to the drawings, in which:

FIG. 7 are statistical interior reconstruction results of low contrast Shepp-Logan phantom. The left column images are the results of using the truncated Hilbert transform that are the initial images of the Statistical interior reconstruction, while the right column images are the results of the Statistical interior reconstruction with TV minimization. The top and bottom rows are respectively the reconstructed images from Poisson projection data with 200,000 and 50,000 photos FIG. 8 is the projection model of a discrete image in fan-beam geometry.

FIG. 9 are reconstructed 128×128 images from projection datasets with Gaussian noise. The first-row images were reconstructed using our newly developed algorithm, while the second-row counterparts were obtained without the sparsity constraint. The 1st, 2nd, 3rd and 4th columns are reconstructed from 55, 45, 35 and 25 projections, respectively. The display window is [0 0.5].

DETAILED DESCRIPTION OF THE PREFERRED EMBODIMENT

Section I. Alternating-Minimization-Based Interior Tomography

I.1. Theoretical Results

Figure 1:
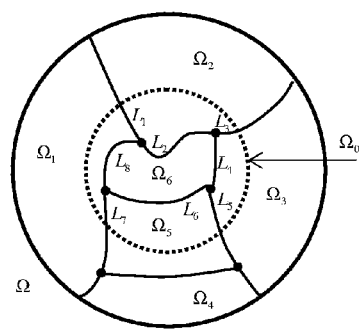
FIG. 1 is an example of piecewise constant function on a compact support.

It is well known that the CS theory depends on the principle of transform sparsity. For an object of interest such as a digital image, we can arrange it as a vector, and in numerous cases there exists an orthonormal basis to make the object sparse in terms of significant transform coefficients. In CS-based image reconstruction, frequently used sparsifying transforms are discrete gradient transforms and wavelet transforms. The discrete gradient sparsifying transform was recently utilized in CT reconstruction. This is because the x-ray attenuation coefficient often varies mildly within organs, and large image variations are usually confined to the borders of tissue structures. A sparse gradient image may also be a good image model in industrial or security applications.

Now, let us analyze the possible exactness of interior tomography in the CS framework subject to the TV minimization. Without loss of generality, let us consider a 2D smooth image $f(\vec{r})=f(x,y)=f(\rho,\theta)$, $\rho \in [0,1]$, $\theta \in [0,2\pi)$ on the compact support unit disk $\Omega$. Its Radon transform can be written as $R(s,\phi)$, $s \in [-1,1]$, $\phi \in [0,\pi)$. Suppose that we are only interested in its interior part $f(\rho,\theta)$ with $\rho < \rho_0$, and we only know the corresponding local Radon transforms $R(s,\phi)$, $|s| < \rho_0$, which is also referred to as local parallel-beam projections. Based on the classic analysis (see F. Natterer, *The mathematics of computerized tomography*. Classics in applied mathematics 2001, Philadelphia: Society for Industrial and Applied Mathematics), in general there is no unique solution if we only know these local data. For any reconstructed image from the local data set, it can be viewed as an exact reconstruction from a complete dataset $R(s,\phi)$, $s \in [-1,1]$, $\phi \in [0,\pi)$ and a global dataset $\tilde{R}(s,\phi)$, $\rho_0 < |s| \leq 1$, $\phi \in [0,\pi)$. Although $\tilde{R}(s,\phi)=0$ for $|s| < \rho_0$, it can still produce a non-zero 2D local image $g(\rho,\theta)$, $\rho \in [0,\rho_0)$, $\theta \in [0,2\pi)$ inside the ROI, which is the reason for the non-uniqueness.

Lemma I.1: For any Radon transform $\tilde{R}(s,\phi)$, $\rho_0 < |s| \leq 1$, $\phi \in [0,\pi)$, the corresponding reconstructed image $g(\rho,\theta)$ with $\rho < \rho_0$ is smooth and bounded if $\tilde{R}(s,\phi)$ is continuous and bounded.

Lemma I.2: For the reconstructed image $g(\rho,\theta)$ with $|\rho|<\rho_0$, both $$\frac{\partial g(\rho,\theta)}{\partial \rho} \text{ and } \frac{\partial g(\rho,\theta)}{\rho\partial\theta}$$

are smooth and bounded.

Theoretically speaking, the L1 norm of the image $f(\rho,\theta)$ inside the ROI can be expressed as:

$$f_{tv} = \int_0^{2\pi} d\theta \int_0^{\rho_0} |\mu(\rho,\theta)|\rho\, d\rho, \qquad (I.1)$$

where $\mu(\rho,\theta)$ represents a sparifying transform. For the commonly used gradient transform in the medical imaging field, we have $$\mu(\rho,\theta) = \sqrt{\left(\frac{\partial f(\rho,\theta)}{\partial \rho}\right)^2 + \left(\frac{\partial f(\rho,\theta)}{\rho\partial\theta}\right)^2}, \qquad (I.2)$$

which is the gradient magnitude or absolute value of the maximum directional derivation at $(\rho,\theta)$. If there is no other statement in this paper, we always assume that $\mu(\rho,\theta)$ defined by Eq. (I.1) and (I.2) represents the total variation. When there exists an artifact image $g(\rho,\theta)$ due to the data truncation, the total variation will be:

$$\tilde{f}_{tv} = \int_0^{2\pi} d\theta \int_0^{\rho_0} \tilde{\mu}(\rho,\theta)\rho\, d\rho \qquad (I.3)$$

$$= \int_0^{2\pi} d\theta \int_0^{\rho_0} \rho$$

$$\sqrt{\left(\frac{\partial f(\rho,\theta)}{\partial \rho}\right) + \lambda\left(\frac{\partial g(\rho,\theta)}{\partial \rho}\right)^2 + \left(\frac{\partial f(\rho,\theta)}{\rho\partial\theta}\right) + \lambda\left(\frac{\partial g(\rho,\theta)}{\rho\partial\theta}\right)^2} \, d\rho,$$

where $\tilde{\mu}(\rho,\theta)$ represents the sparifying transform of a reconstructed image including an artifact image $g(\rho,\theta)$ and $\lambda$ is a coefficient. If we can prove that $\tilde{f}_{tv}$ can be minimized at $\lambda=0$ for the given $f(\rho,\theta)$ and $g(\rho,\theta)$, the exactness of interior tomography in the CS framework should hold in this particular case.

Theorem I.1: In the CS framework, it is impossible to reconstruct exactly an interior ROI of a general 2D smooth function by minimizing the total variation Eq. (I.3).

Lemma I.3. Assuming that a circularly symmetric artifact image $g(\rho,\theta)=g(\rho)$ is reconstructed from a projection dataset $\tilde{R}(s,\phi)=\tilde{R}(s)$ ($|s|\leq 1$, $\phi\in[0,\pi)$) and $\tilde{R}(s)\equiv 0$ for $s\in[-a,a]$. If $g(\rho)$ is a square integrable function on [0,1] with $g(\rho)\equiv C$ ($\rho\in[0,a)$), then $C=0$.

Lemma I.4. Assuming that a circularly non-symmetric artifact image $g(\rho,\theta)$ is reconstructed from a projection dataset $\tilde{R}(s,\phi)$ ($|s|\leq 1$, $\phi\in[0,\pi)$) and $\tilde{R}(s,\phi)\equiv 0$ for $s\in[-a,a]$. If $g(\rho,\theta)$ is a square integrable function on $\rho\in[0,1]$ and $\theta\in[0,2\pi]$ with $g(\rho,\theta)\equiv C$ ($\rho\in[0,a)$), then $C=0$.

Theorem I.2: In the CS framework, an interior ROI of a circular symmetric piecewise constant function $f(\rho)$ can be exactly determined by minimizing the total variation defined in Eq. (I.3).

Next, let us consider a general piecewise constant function $f(\rho,\theta)$ defined on the compact supported unit disk $\Omega$. Without loss of generality, we assume that $\Omega$ can be divided into finite sub-regions $\Omega_n$, $n=1, 2, \ldots, N$, where each sub-region $\Omega_n$ has a non-zero area measure, on which $f(\rho,\theta)$ is a constant. As a result, these sub-regions also define finitely many boundaries in terms of arc-segments, each of which is of a non-zero length and differentiable almost everywhere excluding at most finitely many points. We assume that an interior ROI $\Omega_0$ (defined by $\rho<\rho_0$) covers M boundaries and these line segments are denoted as $L_1, L_2, \ldots L_m \ldots, L_M$. While the length of $L_m$ is denoted as $t_m>0$, the difference between the two neighboring sub-regions is denoted as $q_m$. An example is given in FIG. 1, where the compact support $\Omega$ includes 6 sub-regions and the ROI $\Omega_0$ covers 8 arc-segments as boundaries.

Theorem I.3: In the CS framework, an interior ROI of a general compactly supported function $f(\vec{r})$ can be exactly determined by minimizing the total variation defined by Eq. (I.3) if $f(\vec{r})$ can be decomposed into finitely many constant sub-regions.

All of the above results were proved in our recent publications (see H. Y. Yu, and G. Wang, *Compressed sensing based interior tomography*. Phys Med Biol, 2009. 54(9): p. 2791-2805; H. Y. Yu, et al., *Supplemental analysis on compressed sensing based interior tomography*. Phys Med Biol, 2009. 54(18): p. N425-N432; W. M. Han, H. Y. Yu and G. Wang; *A general total variation minimization theorem for compressed sensing based interior tomography*; International Journal of Biomedical Imaging, Article ID: 125871, 2009, 3 pages). In the same spirit of the published proofs, by defining a different sparifying transform $\mu$, our results can be extended to some interesting families of functions. Particularly, we have proved that if an ROI/VOI is piecewise polynomial, then the ROI/VOI can be accurately reconstructed from projection data associated with x-rays through the ROI/VOI by minimizing the high-order total variation (J. S. Yang, H. Y. Yu, M. Jiang and G. Wang; *High order total variation minimization for interior tomography*, Inverse Problems, 26(3), Article ID: 035013, 2010, 29 pages).

As an important molecular imaging modality, single-photon emission computed tomography (SPECT) is to reconstruct a radioactive source distribution within a patient or animal. Different from the line integral model for x-ray imaging, SPECT projections can be mathematically modeled as an exponentially attenuated Radon transform. In this context, the CT reconstruction may be regarded as a special case of SPECT (all the attenuation coefficients are zeros). Expanding CT interior tomography results, we have proved that accurate and stable the interior SPECT reconstruction of an ROI is feasible from uniformly attenuated local projection data aided by prior knowledge of a sub-region in the ROI. Naturally, the above theoretical results can be extended to SPECT using the same arguments. That is, it is possible to reconstruct a SPECT ROI accurately only from the uniformly attenuated local projections by minimizing the L1 norm of its sparsity transform if the distribution function to be reconstructed is piecewise constant/polynomial. The same methodology can be employed for magnetic resonance imaging.

1.2. OS-SART Based Reconstruction Algorithm

To verify the above theoretical results, we developed a numerical interior tomography algorithm in the CS framework. The algorithm consists of two major steps. In the first step, the ordered-subset simultaneous algebraic reconstruction technique (OS-SART) (G. Wang and M. Jiang, *Ordered-Subset Simultaneous Algebraic Reconstruction Techniques (OS-SART)*, Journal of X-ray Science and Technology, 12:169-77, 2007) was used to reconstruct a digital image $f_{m,n} = f(m\Delta, n\Delta)$ based on all the truncated local projections, where $\Delta$ represents the sampling interval, m and n are integers. In the second step, we minimize the L1 norm for a given sparsifying transform of the discrete image $f_{m,n}$ using the standard steepest descent method. These two steps were iteratively performed in an alternating manner. Specifically, the algorithm can be summarized in the following pseudo-code:

---

S1. Initialize control parameters $\alpha$, $\alpha_s$, $P_{TV}$, and $P_{ART}$;
S2. Initialize reconstruction k := 0 and $f_{m,n}^0 = 0$ ;
S3. Perform OS-SART reconstruction and TV minimization alternately
S3.1 Initialize the loop k := k + 1; $f_{m,n}^k := f_{m,n}^{k-1}$ ;
S3.2 Perform reconstruction for every projection subset $p_{art}$ to $P_{ART}$
S3.2.1 Perform OS-SART reconstruction
S3.2.1.1 Forward compute the current projections of $f_{m,n}^k$ in the $p_{art}$ subset;
S.3.2.1.2 Update $f_{m,n}^k$ by backprojecting the projection errors in the $p_{art}$ subset;
S.3.2.2 Minimize TV by steepest descent method for $p_{tv}$ = 1 to $P_{TV}$ to
S.3.2.2.1 Compute the steepest decent direction $d_{m,n}$ ;
S.3.2.2.2 Compute normalized coefficient $\beta := \max(|f_{m,n}^k|) \div \max(|d_{m,n}|)$;
S.3.2.2.3 Update the reconstructed image $f_{m,n}^k = f_{m,n}^k - \alpha \times \beta \times d_{m,n}$ ;
S.3.2.2.4 Update the control parameter $\alpha = \alpha \times \alpha_s$ ;
S3.3 Check the stopping criteria

---

S1 initializes the control parameters $\alpha$, $\alpha_s$, $P_{TV}$ and $P_{ART}$, where $\alpha$ represents the maximal step for the steepest descent to minimize TV, $\alpha_s$ the decreasing scale of $\alpha$ after each computation, $P_{TV}$ the local loop time to minimize TV, and $P_{ART}$ denotes the number of subsets for OS-SART reconstruction. S2 initializes the reconstructed image and the main loop count k for alternating iteration procedure S3. S3.2.1.1 computes the forward projections of the current image in the $p_{art}$ subset, where it may include both local truncated and global scout projections. In our code, we employ a global imaging geometry and adapt a projection mask image to indicate which pixel in the projection domain is available. S3.2.1.2 updates $f_{m,n}^k$ by backprojecting the projection differences, where only the projections in $p_{art}$ subset are used. S3.2.2 define the local loop to minimize the L1 norm. S3.3 decides if the main loop should be stopped or not.

For the discrete gradient transform, the magnitude of the gradient can be approximately expressed as:

$$\mu_{m,n} \cong \sqrt{\frac{(f_{m+1,n}-f_{m,n})^2 + (f_{m,n}-f_{m-1,n})^2 + (f_{m,n+1}-f_{m,n})^2 + (f_{m,n}-f_{m,n-1})^2}{2\nabla^2}} . \quad (I.10)$$

Correspondingly, the total variation can be defined as $$f_{TV} = \sum_m \sum_n \mu_{m,n}.$$

Then, we have the steepest descent direction defined by $$d_{m,n} = \frac{\partial f_{TV}}{\partial f_{m,n}} \quad (I.11)$$

$$= \frac{4f_{m,n} - f_{m+1,n} - f_{m-1,n} - f_{m,n+1} - f_{m,n-1}}{\mu_{m,n}} +$$

$$\frac{f_{m,n} - f_{m+1,n}}{\mu_{m+1,n}} + \frac{f_{m,n} - f_{m-1,n}}{\mu_{m-1,n}} + \frac{f_{m,n} - f_{m,n+1}}{\mu_{m,n+1}} +$$

$$\frac{f_{m,n} - f_{m,n-1}}{\mu_{m,n-1}}.$$

For others sparsifying transform, we can deduce the corresponding $d_{m,n}$ easily. To avoid the singularity when computing $d_{m,n}$ using Eq. (I.11), we added a small constant $\epsilon$ to Eq. (I.11) when computing the gradient $\mu_{m,n}$. That is, $$\mu_{m,n} \cong \sqrt{\frac{(f_{m+1,n}-f_{m,n})^2 + (f_{m,n}-f_{m-1,n})^2 + (f_{m,n+1}-f_{m,n})^2 + (f_{m,n}-f_{m,n-1})^2}{2\nabla^2} + \varepsilon^2} . \quad (I.12)$$

Figure 2:
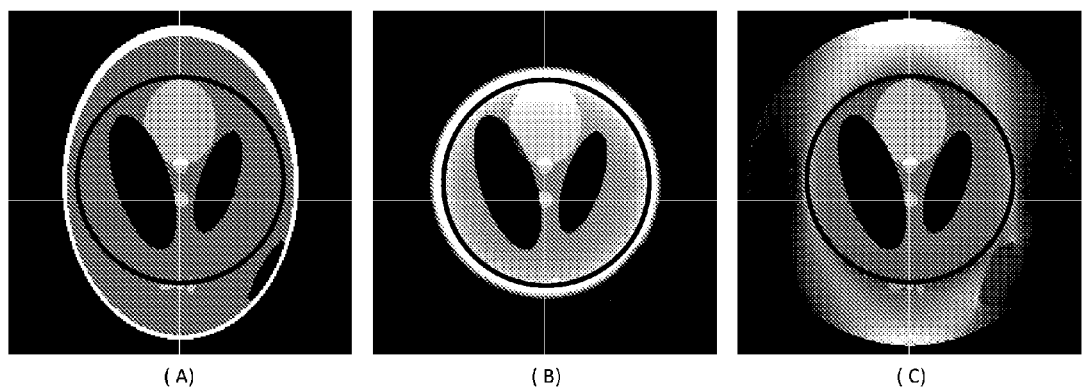
FIG. 2 shows the reconstructed images of a modified Shepp-logan phantom after 60 iterations. (A) is the original phantom, (B) the reconstruction using the local FBP (after smooth data extrapolation), and (C) the reconstruction using the proposed CS-based interior tomography algorithm. The display window is [0.1, 0.4].
Figure 3:
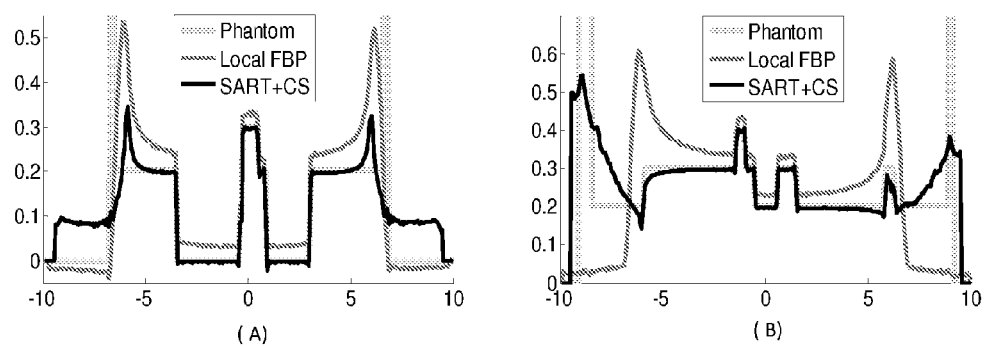
FIG. 3 are typical profiles along the white lines in FIG. 2.

In our numerical simulation, we assumed a circular scanning locus of radius 57.0 cm and a fan-beam imaging geometry. We also assumed an equi-spatial virtual detector array of length 12.0 cm. The detector was centered at the system origin and made always perpendicular to the direction from the system origin to the x-ray source. The detector array included 360 elements, each of which is of aperture 0.033 cm. This scanning configuration covered a circular FOV of radius 5.967 cm. For a complete scanning turn, we equi-angularly collected 1300 projections. The reconstructed object was a 2D modified Shepp-logan phantom. This phantom is piecewise constant and includes a set of smooth ellipses whose parameters are listed in Table 1, where a,b represent the x,y semi-axes, $(x_0, y_0)$ the center of the ellipse, $\omega$ denotes the rotation angle, $f$ the relative attenuation coefficient. The units for a,b and $(x_0, y_0)$ are cm. The reconstructed images were in a 256×256 matrix covering an FOV of radius 10 cm. The 60 iterations took 60 minutes. For comparison, we also reconstructed an image using a local FBP method with smooth extrapolation from the truncated projections into missing data. Some typical reconstructed images were shown in FIG. 2. The typical profiles were in FIG. 3. As seen from FIGS. 2 and 3, the reconstructed images from the proposed algorithm are in a high precision inside the ROI.

TABLE 1

Parameters of the 2D modified Shepp-Logan phantom.

| No. | a | b | $x_0$ | $y_0$ | $\omega$ | f |
|---|---|---|---|---|---|---|
| 1 | 6.900 | 9.200 | 0 | 0 | 0 | 1.0 |
| 2 | 6.624 | 8.740 | 0 | −0.184 | 0 | −0.8 |
| 3 | 1.100 | 3.100 | 2.200 | 0 | −18. | −0.2 |
| 4 | 1.600 | 4.100 | −2.200 | 0 | 18.0 | −0.2 |
| 5 | 2.100 | 2.500 | 0 | 3.500 | 0 | 0.1 |
| 6 | 0.460 | 0.460 | 0 | 1.000 | 0 | 0.1 |
| 7 | 0.460 | 0.460 | 0 | −0.100 | 0 | 0.1 |
| 8 | 0.460 | 0.230 | −0.800 | −6.050 | 0 | 0.1 |
| 9 | 0.230 | 0.230 | 0 | −6.060 | 0 | 0.1 |
| 10 | 0.230 | 0.460 | 0.600 | −6.060 | 0 | 0.1 |
| 11 | 2.000 | 0.400 | 5.000 | −5.200 | 60.5 | −0.2 |

Figure 4:
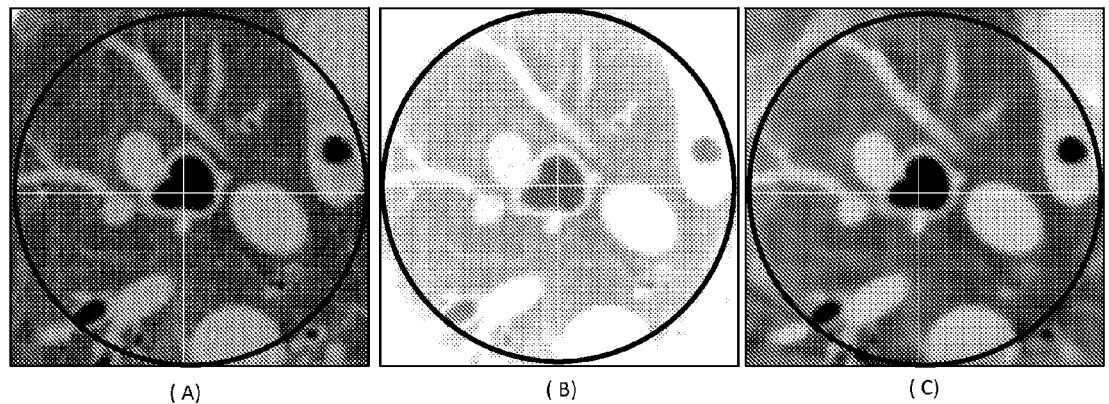
FIG. 4 are reconstructed images from a sheep chest CT scan after 60 iterations. (A) The image reconstructed using FBP from complete projections, (B) the reconstruction using local FBP (after smooth data extrapolation), and (C) the reconstruction using the proposed CS-based interior tomography algorithm. The display window is [−800 HU, 700 HU].

To demonstrate the real-world application of the proposed algorithm, we performed a CT scan of a living sheep, which was approved by Virginia Tech IACUC committee. The chest of a sheep was scanned in fan-beam geometry on a SIEMENS 64-Slice CT scanner (100 kVp, 150 mAs). The x-ray source trajectory of radius 57.0 cm was used. There were 1160 projections uniformly collected over a 360° range, and 672 detectors were equi-angularly distributed per projection. Thus, the FOV of radius 25.05 cm was formed. First, an entire 29.06 cm by 29.06 cm cross-section was reconstructed into 1024×1024 pixels using the popular FBP method from a complete dataset of projections. Second, a trachea was selected in reference to the reconstructed image. Around the trachea, a circular ROI of radius 120 pixels was specified. Then, only the projection data through the ROI were kept to simulate an interior scan. Third, the ROI was reconstructed by the local FBP with smooth data extrapolation and our proposed algorithms, respectively. The results were in FIG. 4. Comparing the images in FIG. 4, we observe that the proposed algorithm not only keeps image accuracy but also suppresses image noise.

Figure 5:
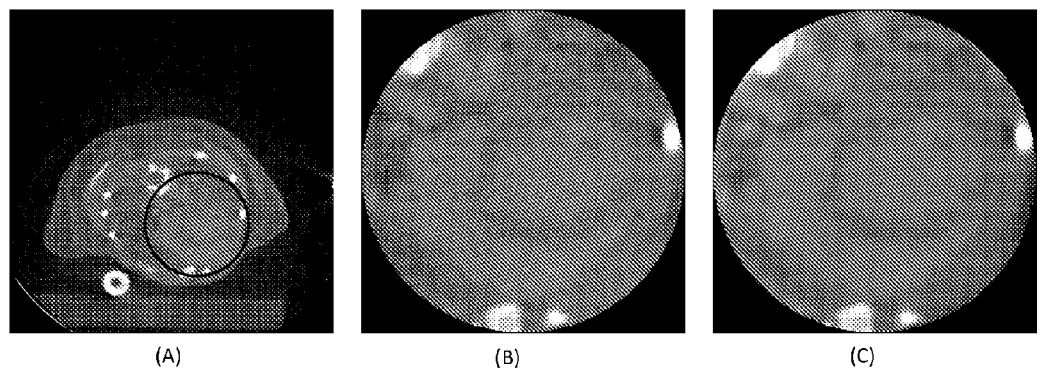
FIG. 5 are compressive-sampling-based interior tomography of a mouse chest using the CNT-based x-ray source gating technique. (A) The image reconstructed from a complete global dataset as the gold standard with the white circle for a cardiac ROI, (B) the local magnification of the ROI in (A) and (C) the interior tomography reconstruction from 400 projections after 60 iterations (without precise knowledge of a subregion in the ROI).

In vivo mouse imaging experiments were also performed following the protocols approved by the University of North Carolina at Chapel Hill. Projection images were acquired using a prospective gating approach. For CT scans carried out in this study, 400 projections were acquired over a circular orbit of 199.5 degrees with a stepping angle of 0.5 degree at single frame acquisition. By running the detector at 1 frame/sec (camera integration time=500 ms), the scan time was 15-30 min, depending the mouse's respiration and heart rates. For the above acquired in vivo mouse cardiac projection datasets, we performed a CS-based interior reconstruction. Using the generalized Feldkamp algorithm (see L. A. Feldkamp, L. C. Davis, and J. W. Kress, *Practical cone-beam algorithm*. J. Opt. Soc. Am., 1984. 1(A): p. 612-619; G. Wang, et al., *A General Cone-Beam Reconstruction Algorithm*. IEEE Transactions on Medical Imaging, 1993. 12(3): p. 486-496), first we reconstructed a volumetric image to serve as a global standard for our interior reconstruction. From such an image volume, we specified a circular ROI on a transverse slice to cover the contrast-enhanced beating heart. Then, we created a mask image for the ROI and performed a forward projection to generate a mask projection. Later the mask projection was binarized to extract the projection data only through the ROI as our interior scan dataset. Meanwhile, the global projections of $1^{st}$ and $360^{th}$ were kept to serve as two scout images. The interior reconstruction was performed using our CS based algorithm described in section II; the control parameters were α=0.005, $α_s$=0.997, $P_{TV}$=2, and $P_{ART}$=20. The final reconstruction results are in FIG. 5. Because the CS-based iterative reconstruction framework is capable of noise removing, our CS-based interior reconstruction result has a high SNR than that of the global FBP reconstruction.

Figure 6:
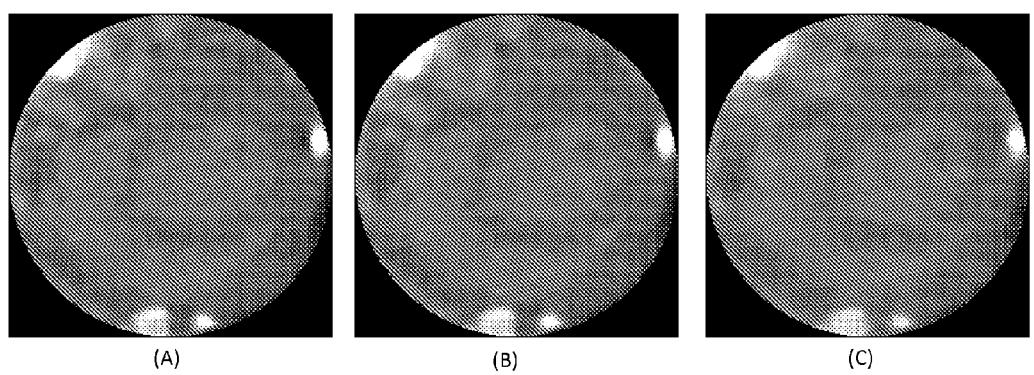
FIG. 6 are compressive-sampling-based interior tomography of a mouse chest using (A) 200, (B) 100 and (C) 50 projections to reduce the radiation dose to 50%, 25% and 12.5% of that for FIG. 5(C), respectively.

While the radiation dose to the whole body can be reduced using our reconstruction method by limiting the x-ray beam to the ROI only, the organ dose—the dose of the organ which happens to be within the ROI under interior reconstruction—would remain at the same level. Because the CS reconstruction theory is based on the so-called sparsifying transform, the radiation dose of local ROI can be further reduced with fewer projection views. However, the smaller the number of projections, the worse the reconstructed image quality (see Chen, G. H., J. Tang, and S. Leng, *Prior image constrained compressed sensing (PICCS): A method to accurately reconstruct dynamic CT images from highly undersampled projection data sets*. Medical Physics, 2008. 35(2): p. 660-663). To study how the projection number affects the reconstructed image quality, 200/100/50 projections were uniformly selected from the above mentioned projections by discarding 1/3/7 projections in every 2/4/8/ projections. For these reduced projections, we can save radiation dose 50%, 75% and 87.5%, respectively. During the reconstruction procedure, two global orthogonal scout projections were also employed. The reconstructed results are shown in FIG. 6. It can be seen that the image quality was good enough even using only 100 projections.

I.3. Statistical Interior Reconstruction Algorithm

In fact, our CS-based interior reconstruction can also be implemented in a statistical framework (Q. Xu, H. Y. Yu, X. Q. Mou and G. Wang, *A statistical reconstruction method for interior problem*, Proceedings of SPIE, to appear in August 2010). We have implemented PWLS, q-GGMRF, SIRTV, and OSSART-TV algorithm. Moreover, we changed the OSSART term of the OSSSART-TV algorithm with an OSWLS term considering the statistical property of projection data. Global and truncated projection data which are both noiseless and noisy (obeying Poisson distribution) were used to test these algorithms.

According to work by Sauer and Bouman (K. Sauer and C. Bouman, *A local updated strategy for iterative reconstruction from projections*, IEEE Transactions on Signal Processing, 41(2):534-548, 1993), the specific update iteration of the quadratic PWLS algorithm can be expressed as follows:

$$\mu_j^{n+1} = \mu_j^n + \frac{\sum_i d_i A_{ij}\left(y_i - \sum_k A_{ik}\mu_k^n\right) + \beta \sum_{k \in N_j} w_{jk}(\mu_k^n - \mu_j^n)}{\sum_i d_i A_{ij}^2 + \beta \sum_{k \in N_j} w_{jk}}, \quad (I.13)$$

where $\mu_j^n$ denotes the value of the jth voxel after the nth iteration, $d_i$ represent the maximum likelihood estimates of the inverse of the variance of the projection data, β is the penalty parameter, and $N_j$ denotes the neighborhood of the pixel j and $w_{jk}$ are the directional weighting coefficients.

According to the paper by J. B. Thibault et al (J. B. Thibault et al, *A three-dimensional statistical approach to improve image quality for multi-slice helical CT*, Medical Physics, 34(11): 4526-4544, 2007), the specific optimization of the q-GGMRF algorithm is:

$$\hat{\mu}_j^{n+1} = \operatorname{argmin}\left\{\sum_i \frac{d_i}{2}\left(y_i - \sum_k A_{ik}\mu_k^n + A_{ij}(\mu_j^n - \mu_j)\right)^2 + \beta \sum_{\{j,k\} \in C} w_{jk} \frac{|\mu_j - \mu_k|^p}{1 + \left|\frac{\mu_j - \mu_k}{c}\right|^{p-q}}\right\}, \quad (I.14)$$

According to the paper by J. Tang et al (J. Tang, et al, *Performance comparison between total variation based compressed sensing and statistical iterative reconstruction algorithm*, Physics in Medicine and Biology, 54(19):5781-5804, 2009), the optimization method of the SIRTV algorithm is similar to the q-GGMRF algorithm. And we have $$\hat{\mu}_j^{n+1} = \operatorname{argmin}\left\{\sum_i \frac{d_i}{2}\left(y_i - \sum_k A_{ik}\mu_k^n + A_{ij}(\mu_j^n - \mu_j)\right)^2 + \beta TV(\mu)\right\}, \quad (I.15)$$

where $\mu_j = \mu_{m,n}$.

Notice that Gauss-Seidel method is adopted in the implementations of the above three algorithms. Voxels are updated in a random but fixed order. The half-interval search is used to find the root of the derivative.

In our implementation, the measurements are assumed to follow Poisson statistical model, and the reconstruction process is to maximize the object function with a prior of total variation (TV) minimization or L1 norm minimization. In order to increase the accuracy and stability of this algorithm, a small known sub-region in the ROI is needed. The rough result of the inversion of the truncated Hilbert transform with the small known sub-region is regard as the initial image of the statistical TV iteration. In the numerical simulation experiment, we evaluated the anti-noise property of our algorithm at different dose level (FIG. 7).

Section II. Soft-Thresholding-Based Methods

II.1. Mathematical Principal

Daubechies and her collaborators proposed a general iterative thresholding algorithm to solve linear inverse problems regularized by a sparsity constraint and proved its convergence (see I. Daubechies, M. Defrise, and C. De Mol, *An iterative thresholding algorithm for linear inverse problems with a sparsity constraint*. Communications on Pure and Applied Mathematics, 2004. 57(11): p. 1413-1457; I. Daubechies, M. Fornasier, and I. Loris, *Accelerated projected gradient method for linear inverse problems with sparsity constraints*. Journal of Fourier Analysis and Applications, 2008. 14(5-6): p. 764-792). Their approach can be directly applied for the CT reconstruction from a limited number of projections. Their major results can be summarized as follows.

Let $f=[f_1, f_2, \ldots, f_N]^T \in \mathbb{R}^N$ be an object function and $g=[g_1, g_2, \ldots, g_M]^T \in \mathbb{R}^M$ be a set of measurements. Usually, they are linked by:

$$g = Af + e, \quad (II.1)$$

where $A=(a_{mn}) \in \mathbb{R}^M \times \mathbb{R}^N$ is the linear measurement matrix, and $e \in \mathbb{R}^M$ the measurement noise. Let us define the $l_p$ norm of the vector g as $$\|g\|_p = \left(\sum_{m=1}^M g_m^p\right)^{1/p}. \quad (II.2)$$

In practical applications, we usually omit the subscript p when p=2. To find an estimate of f from g, one can minimize the discrepancy $\Delta(f)$ $$\Delta(f) = \|g - Af\|^2. \quad (II.3)$$

When the system (II.1) is ill-posed, the solution to Eq. (II.3) is not satisfactory, and additional constraints are required to regularize the solution. Particularly, given a complete basis $(\phi_\gamma)_{\gamma \in \Gamma}$ of the space $\mathbb{R}^N$ satisfying $$f = \sum_{\gamma \in \Gamma} \langle f, \varphi_\gamma \rangle \varphi_\gamma,$$

and a sequence of strictly positive weights $w=(w_\gamma)_{\gamma \in \Gamma}$, we define the functional $\Phi_{w,p}(f)$ by $$\Phi_{w,p}(f) = \Delta(f) + \sum_{\gamma \in \Gamma} 2w_\gamma |\langle f, \varphi_\gamma \rangle|^p, \quad (II.4)$$

where $\langle \bullet, \bullet \rangle$ represents the inner product and $1 \leq p \leq 2$. Using the $l_p$ norm definition (II.2), let us define the $l_p$ norm of a matrix operator A as $$\|A\|_p = \max_{f \neq 0} \left(\frac{\|Af\|_p}{\|f\|_p}\right). \quad (II.5)$$

Let $A^T$ be the adjoint operator of A, which is the transpose matrix of A, the operator A in (II.1) be bounded, and $\|A^TA\| < C$. In the following, we will assume C=1 because A can always be re-normalized. To find an estimate of f from g under the $l_p$ norm regularization term $$\sum_{\gamma \in \Gamma} 2w_\gamma |\langle f, \varphi_\gamma \rangle|^p,$$

we can minimize $\Phi_{w,p}(f)$ defined in (II.4). The minimizer of $\Phi_{w,p}(f)$ can be recursively determined by the soft-thresholding algorithm:

$$f^k = \mathbb{S}_{w,p}(f_{k-1} + A^T(g - Af^{k-1})), \quad (II.6)$$

where k=1, 2, ... is the iteration number, $f^0$ the initial value in $\mathbb{R}^N$, and $$\mathbb{S}_{w,p}(f) = \sum_{\gamma \in \Gamma} S_{w_\gamma, p}(\langle f, \varphi_\gamma \rangle) \varphi_\gamma, \quad (II.7)$$

with $S_{w,p} = (F_{w,p})^{-1}$ is a one-to-one map from $\mathbb{R}$ to its self for p>1 with $$F_{w,p}(x) = x + wp \, sgn(x) |x|^{p-1}. \quad (II.8)$$

Particularly, $$S_{w,3/2}(x) = \begin{cases} x - \dfrac{3w(\sqrt{9w^2 + 16|x|} - 3w)}{8} & \text{if } x \geq 0 \\ x + \dfrac{3w(\sqrt{9w^2 + 16|x|} - 3w)}{8} & \text{if } x < 0 \end{cases}. \quad (II.9)$$

When p=1, we can set $$S_{w,1}(x) = \begin{cases} x - w & \text{if } x \geq w \\ 0 & \text{if } |x| < w \\ x + w & \text{if } x \leq -w \end{cases}. \quad (II.10)$$

The main result of Daubechies et al. (I. Daubechies, M. Defrise, and C. De Mol, *An iterative thresholding algorithm for linear inverse problems with a sparsity constraint*. Communications on Pure and Applied Mathematics, 2004. 57(11): p. 1413-1457) is that the solution of (II.6) is convergent.

Unfortunately, the convergence speed of Eq. (II.6) is very slow. To facilitate practical applications, an accelerated projected gradient method was then developed (I. Daubechies, M. Fornasier, and I. Loris, *Accelerated projected gradient method for linear inverse problems with sparsity constraints*. Journal of Fourier Analysis and Applications, 2008. 14(5-6): p. 764-792). When $w_\gamma = \tau$ for all $\gamma \in \Gamma$, $\Phi_{w,p}(f)$ can be rewritten as $$\Phi_{w,p}(f) = \Phi_{\tau,p}(f) = \Delta(f) + \sum_{\gamma \in \Gamma} 2\tau |\langle f, \varphi_\gamma \rangle|^p. \quad (II.11)$$

Denote the minimizer of Eq. (II.11) as f* and define $$R(f^*, p) = \left(\sum_{\gamma \in \Gamma} |\langle f^*, \varphi_\gamma \rangle|^p\right)^{1/p}, \quad \text{(II.12)}$$

which is the $l_p$ norm radius of f* in the sparse space, we have the accelerated projected gradient algorithm $$f^k = \mathbb{P}_{R(f^*, p)}(f^{k-1} + \beta^k r^k), \quad \text{(II.13)}$$

where $r^k = A^T(g - Af^{k-1})$, $\beta^k = \frac{\|r^k\|^2}{\|Ar^k\|^2}$, and $$\mathbb{P}_{R(f^*, p)}(f) = \mathbb{S}_{\mu,p}(f) = \sum_{\gamma \in \Gamma} S_{\mu,p}(\langle f, \varphi_\gamma \rangle)\varphi_\gamma, \quad \text{(II.14)}$$

with an adapted soft-threshold $\mu = \mu(R(f^*,p),f)$ depending on $R(f^*,p)$ and f. When $R(f,p) \leq R(f^*,p)$, $\mu(R(f^*,p),f)=0$ and $(\mathbb{P}_{R(f^*,p)})(f)=f$. When $R(f,p)>R(f^*,p)$, the adapted threshold $\mu$ should be chosen to satisfy $$R((\mathbb{P}_{R(f^*,p)}(f),p)=R(\mathbb{S}_{\mu,p}(f),p)=R(f^*,p). \quad \text{(II.15)}$$

Regarding the algorithm (II.13), we have several comments in order.

First, although Daubechies et al. only proved the convergence for the case p=1, we believe that it should stand for $1 \leq p \leq 2$. Second, while we have previously assumed that $\|A^T A\| < C$ and C=1, it can be proved that the algorithm (II.13) holds for any positive C. Third, it is generally impossible to know the exact value of R(f*,p) but we can have an approximate estimate.

II.2. SART-Type Algorithm

In the context of image reconstruction, each component of the function f in Eq. (II.1) is interpreted as an image pixel with N being the total pixel number. Each component of the function g is a measured datum with M being the product of the number of projections and the number of detector elements. In fan-beam geometry with a discrete image grid, the $n^{th}$ pixel can be viewed as a rectangular region with a constant value $f_n$, the $m^{th}$ measured datum $g_m$ as an integral of areas of pixels partially covered by a narrow beam from an x-ray source to a detector element and respectively weighted by the corresponding x-ray linear attenuation coefficients. Thus, the component $a_{mn}$ in Eq. (II.1) can be understood as the interaction area between the $n^{th}$ pixel and the $m^{th}$ fan-beam path (FIG. 8). While the whole matrix A represents the forward projection, $A^T$ implements the back projection. The SART-type solution to Eq. (II.1) can be written as:

$$f_n^k = f_n^{k-1} + \lambda^k \frac{1}{a_{+n}} \sum_{m=1}^{M} \frac{a_{mn}}{a_{m+}}(g_m - A_m f^{k-1}), \quad \text{(II.16)}$$

where $$a_{+n} = \sum_{m=1}^{M} a_{mn} > 0, \quad a_{m+} = \sum_{n=1}^{N} a_{mn} > 0,$$

$A_m$ is the $m^{th}$ row of A, k the iteration index, and $0 < \lambda^k < 2$ a free relaxation parameter. Let $\Lambda^{+N} \in \mathbb{R}^N \times \mathbb{R}^N$ be a diagonal matrix with $$\Lambda_{nn}^{+N} = \frac{1}{a_{+n}}$$

and $\Lambda^{M+} \in \mathbb{R}^M \times \mathbb{R}^M$ be a diagonal matrix with $$\Lambda_{mm}^{M+} = \frac{1}{a_{m+}}, \quad \text{Eq. (II.16)}$$

can be rewritten as:

$$f^k = f^{k-1} + \lambda^k \tilde{r}^k, \quad \text{(II.17)}$$

with $$\tilde{r}^k = \Lambda^{+N} A^T \Lambda^{M+}(g - Af^{k-1}). \quad \text{(II.18)}$$

Due to the introduction of $\Lambda^{+N}$ and $\Lambda^{M+}$, Eq. (II.18) cannot be directly applied to solve Eq. (II.13). However, we can modify Eq. (II.18) to obtain a new $r^k$ defined as $$r^k = \frac{\|A^T\|}{\|\Lambda^{+N} A^T \Lambda^{M+}\|} \tilde{r}^k = \alpha \tilde{r}^k. \quad \text{(II.19)}$$

Substituting Eq. (II.19) into Eq. (II.13), we have a SART-type algorithm $$f^k(\mathbb{P}_{R(f^*,p)}(f^{k-1} + \alpha \beta^k \tilde{r}^k), \quad \text{(II.20)}$$

with $$\beta^k = \frac{\|\tilde{r}^k\|}{\|A\tilde{r}^k\|^2}.$$

The heuristic rationale for the above modification is to incorporate the SART-type weighting scheme for a more uniform convergence behavior. $\alpha$ can be written as $$\alpha^2 = \frac{\max_{1 \leq n \leq N}(A^T A I)}{\max(\|\Lambda^{+N} A^T \Lambda^{M+} \Lambda^{M+} A \Lambda^{+N} I\|)} \alpha_0^2 \quad \text{(II.21)}$$

with $$\alpha_0^2 = \frac{\max_{1 \leq n \leq N}(\Lambda^{+N} A^T \Lambda^{M+} \Lambda^{M+} A \Lambda^{+N} I)}{\|\Lambda^{+N} A^T \Lambda^{M+}\| \cdot \|\Lambda^{M+} A \Lambda^{+N}\|} \frac{\|A^T\| \cdot \|A\|}{\max_{1 \leq n \leq N}(A^T A I)}. \quad \text{(II.22)}$$

In practical applications, we can set $\alpha_0$ to a reasonably large constant such as 2.0 in our simulation in the next section. If the algorithm does not converge, we can reduce $\alpha_0$ until the algorithm converges.

For a basis $(\phi_\gamma)_{\gamma \in \Gamma}$ of the space $\mathbb{R}^N$, in which f has a sparse representation. Our SART-type CT algorithm regularized by sparsity can be summarized in the following pseudo-code:

S1. Initialize $\alpha_0$, $f^{(0)}$ and k;
S2. Estimate R(f*, p);
S3. Pre-compute $\alpha$, $a_{+n}$ and $a_{m+}$;
S4. Update the current estimation iteratively:
S4.1. k := k + 1;
S4.2. $\tilde{r}_k := \Lambda^{+N} A^T \Lambda^{M+}(g - Af^{k-1})$;

-continued $$S.4.3. \beta^k := \frac{\|\tilde{r}^k\|^2}{\|A\tilde{r}^k\|^2};$$

S.4.4. $\tilde{f}^k := f^{k-1} + \alpha\beta^k\tilde{r}^k$;
S.4.5. Compute the sparse transform $\phi_\gamma := \langle \tilde{f}^k, \phi_\gamma \rangle$ for $\gamma \in \Gamma$;
S.4.6. Estimate the adapted threshold $\mu$;
S.4.7. Perform the soft-thresholding $\tilde{\phi}_\gamma := S_{\mu,p}(\phi_\gamma)$;

S.4.8. Perform the inverse sparse transform $f^k := \sum_{\gamma \in \Gamma} \tilde{\phi}_\gamma \varphi_\gamma$;

S.5. Go to S.4 until certain convergence criteria are satisfied.

In the above pseudo-code, S.4.5 represents a sparse transform in a basis $(\phi_\gamma)_{\gamma \in \Gamma}$. It can be either orthonormal (e.g. Fourier transform) or non-orthonormal, and $\phi_\gamma$ is the corresponding coefficient in the sparse space. In S.4.6, the adapted threshold $\mu$ can be estimated by a dichotomy searching method. S.4.7 performs the inverse sparse transform. Finally, the stopping criteria for S.5 can be either the maximum iteration number is reached or the relative reconstruction error (RRE) comes under a pre-defined threshold:

$$E^k = \frac{\|f^k - f^*\|}{f^*} \times 100. \qquad (II.23)$$

Figure 10:
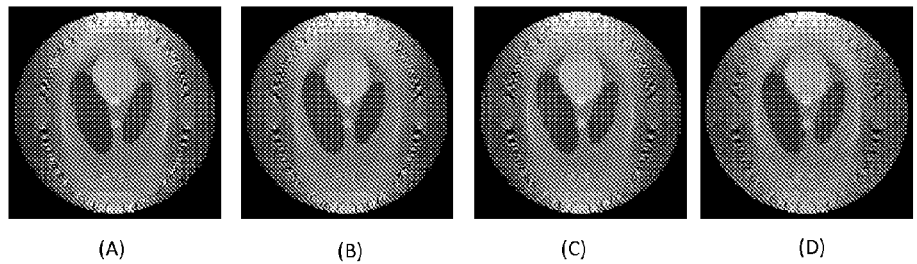
FIG. 10 are interior reconstruction results from truncated datasets with (A) 255, (B) 165, (C) 85 and (D) 45 projections, respectively. The display window is [0 0.5].

The above-proposed algorithm was implemented in MatLab subject to a sparsity constraint in terms of an invertible wavelet transform. The algorithm was implemented with an exemplary Haar wavelet transform and tested with a modified Shepp-Logan phantom. In our simulation, a 128×128 phantom image was in a compact support of radius 10 cm. An equi-spatial detector array was of length 20 cm. The array was centered at the system origin and made perpendicular to the direction from the origin to the x-ray source. The array consisted of 128 elements. While the number of phantom image pixels was 16384, there were only 1708 non-zero wavelet coefficients. For each of selected numbers of projections over a full-scan, the corresponding projection dataset was acquired based on a discrete projection model and a Gaussian noise model. The reconstructed images are in FIG. 9. Then, this approach was applied for interior tomography with a detector array of length 10 cm to produce the corresponding results in FIG. 10.

II.3. Pseudo-Inverses of DGT and DDT

Figure 11:
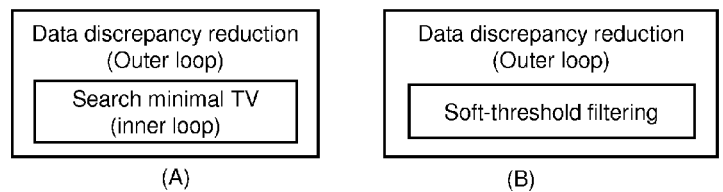
FIG. 11 are the implementation frameworks of (A) traditional and (B) soft-threshold filtering methods for total variation minimization.

The discrete gradient transform (DGT) has been widely utilized as a sparsifying operator in CS-inspired CT reconstruction. This kind of algorithms can be divided into two major steps (FIG. 11 (a)). In the first step, an iteration formula (e.g. SART) is used to update a reconstructed image for data discrepancy reduction. In the second step, a search method (e.g. the standard steepest descent technique) is used in an iterative framework for TV minimization. These two steps need to be iteratively performed in an alternating manner. However, there are no standard stopping and parameter selection criteria for the second step. Usually, these practical issues are addressed in an Ad hoc fashion. On the other hand, soft-threshold nonlinear filtering was proved to be a convergent and efficient algorithm for the $l_1$ norm minimization regularized by a sparsity constraint. Unfortunately, because the DGT is not invertible, it does not satisfy the restricted isometry property (RIP) required by the CS theory and soft-threshold algorithm. In other words, the soft-threshold algorithm cannot be directly applied for TV minimization. Motivated by this challenge, here we construct two pseudo-inverse transforms and apply the soft-threshold filtering for image reconstruction from a limited number of projections.

Let us assume that a digital image satisfies the so-called Neumann conditions on the boundary:

$f_{0,j}=f_{1,j}$ and $f_{I,j}=f_{I+1,j}$ for $1 \leq j \leq J$, $f_{i,0}=f_{i,1}$ and $f_{i,J}=f_{i,J+1}$ for $1 \leq i \leq I$. (II.24)

Then, the standard isotropic discretization of TV can be expressed as $$TV(f) = \sum_{i=1}^{I}\sum_{j=1}^{J} d_{i,j}, \qquad (II.25)$$

$$d_{i,j} = \sqrt{(f_{i,j} - f_{i+1,j})^2 + (f_{i,j} - f_{i,j+1})^2}.$$

We re-write Eq. (II.4) for CT reconstruction problem under the constraint of sparse gradient transform as $$\Phi_{w,1}(f) = \Delta(f) + 2wTV(f). \qquad (II.26)$$

Note that there does not exist a frame such that $d_{i,j} = \langle f, \Phi_{i,j} \rangle$, the solution Eq. (II.6) can not be directly applied to minimize $\Phi_{w,1}(f)$ defined by Eq. (II.25). However, we can construct a pseudo-inverse of the DGT as follows. Assume that $$\tilde{f}_n^k = f_n^{k-1} + \lambda^k \frac{1}{a_{+n}} \sum_{m=1}^{M} \frac{a_{m,n}}{a_{m+}}(g_m - A_m f^{k-1}), \qquad (II.27)$$

is the update from the projection constraint in the current iteration step k, which is exactly the same as Eq. (II.16). We can compute $$d_{i,j}^k = \sqrt{(\tilde{f}_{i,j}^k - \tilde{f}_{i+1,j}^k)^2 + (\tilde{f}_{i,j}^k - \tilde{f}_{i,j+1}^k)^2}. \qquad (II.28)$$

According to the soft-threshold operation in Eq. (II.10), when $d_{i,j}^k < w$ we can adjust the value of $\tilde{f}_{i,j}^k$, $\tilde{f}_{i+1,j}^k$ and $\tilde{f}_{i,j+1}^k$ to make $d_{i,j}^k = 0$, and when $d_{i,j}^k \geq w$ we can reduce the values of $(\tilde{f}_{i,j}^k - \tilde{f}_{i+1,j}^k)^2$ and $(\tilde{f}_{i,j}^k - \tilde{f}_{i,j+1}^k)^2$ to perform the filtering. That is, we can construct the following pseudo-inverse:

$$f_{i,j}^k = \frac{1}{4}(2f_{i,j}^{k,a} + f_{i,j}^{k,b} + f_{i,j}^{k,c}), \qquad (II.29)$$

$$f_{i,j}^{k,a} = \begin{cases} \dfrac{2\tilde{f}_{i,j}^k + \tilde{f}_{i+1,j}^k + \tilde{f}_{i,j+1}^k}{4}, & \text{if } d_{i,j}^k < w \\ \tilde{f}_{i,j}^k - \dfrac{w(2\tilde{f}_{i,j}^k - \tilde{f}_{i+1,j}^k - \tilde{f}_{i,j+1}^k)}{4d_{i,j}^k}, & \text{if } d_{i,j}^k \geq w, \end{cases} \qquad (II.30)$$

$$f_{i,j}^{k,b} = \begin{cases} \dfrac{\tilde{f}_{i,j}^k + \tilde{f}_{i-1,j}^k}{2}, & \text{if } d_{i-1,j}^k < w \\ \tilde{f}_{i,j}^k - \dfrac{w(\tilde{f}_{i,j}^k - \tilde{f}_{i-1,j}^k)}{2d_{i-1,j}^k}, & \text{if } d_{i-1,j}^k \geq w, \end{cases} \qquad (II.31)$$

$$f_{i,j}^{k,c} = \begin{cases} \dfrac{\tilde{f}_{i,j}^k + \tilde{f}_{i,j-1}^k}{2}, & \text{if } d_{i,j-1}^k < w \\ \tilde{f}_{i,j}^k - \dfrac{w(\tilde{f}_{i,j}^k - \tilde{f}_{i,j-1}^k)}{2d_{i,j-1}^k}, & \text{if } d_{i,j-1}^k \geq w. \end{cases} \qquad (II.32)$$

In summary, we have a soft-threshold algorithm for the TV minimization in the following pseudo-code (FIG. 11(b)):

> S1: Initialize the parameters k, w;
> S2: Update the current reconstruction using Eq.(II.16);
> S3: Perform the non-linear filter using Eq.(II.29);
> S4: Go to S2 until the stopping criterion is met.

In addition to the DGT, there are other possible sparse transforms. For example, we can define a total difference (TD) of f as $$TD(f) = \sum_{i=1}^{I} \sum_{j=1}^{J} d_{i,j}, \quad d_{i,j} = |f_{i,j} - f_{i+1,j}| + |f_{i,j} - f_{i,j+1}|, \quad (II.33)$$

and rewrite Eq. (II.4) as $$\Phi_{w,1}(f) = \Delta(f) + 2wTD(f). \quad (II.34)$$

We call $d_{i,j}$ in Eq. (II.33) a discrete difference transform (DDT). Similar to what we have done for DGT, after the soft-threshold filtering, we can construct a pseudo-inverse of $f_{i,j}^k$ as $$f_{i,j}^k = \frac{1}{4}(q(w, \tilde{f}_{i,j}^k, \tilde{f}_{i+1,j}^k) + q(w, \tilde{f}_{i,j}^k, \tilde{f}_{i,j+1}^k) + \quad (II.35)$$
$$q(w, \tilde{f}_{i,j}^k, \tilde{f}_{i,j-1}^k) + q(w, \tilde{f}_{i,j}^k, \tilde{f}_{i-1,j}^k)),$$

$$q(w, y, z) = \begin{cases} \frac{y+z}{2}, & \text{if } |y-z| < w \\ y - \frac{w}{2}, & \text{if } (y-z) \geq w \\ y + \frac{w}{2}, & \text{if } (y-z) \leq -w. \end{cases} \quad (II.36)$$

That is, we have a soft-threshold algorithm for TD minimization in the following pseudo-code:

> S1: Initialize the parameters k, w;
> S2: Update the current reconstruction using Eq.(II.16);
> S3: Perform the non-linear filter using Eq.(II.36);
> S4: Go to S2 until the stopping criterion is met.

To facilitate practical applications, an accelerated projected gradient method can directly develop to automatically select the parameters w for the above soft-threshold filtering operations to minimize the TD and TV. And all of those results can be directly used for interior reconstruction.

Figure 12:
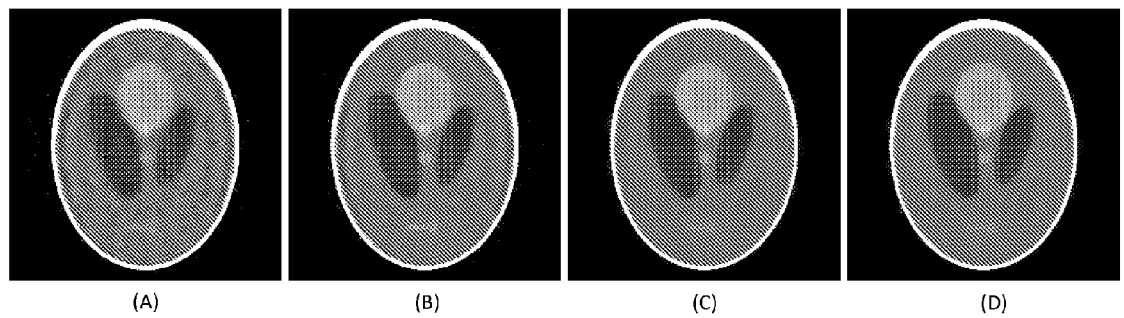
FIG. 12 are reconstructions from 21 noise-free projections. (A) The reconstruction using the SART method without the TV minimization, (B) using the steepest descent method for the TV minimization, (C) and (D) using the soft-threshold filtering methods for the TV and TD minimization, respectively. The display window is [0,0.5].
Figure 13:
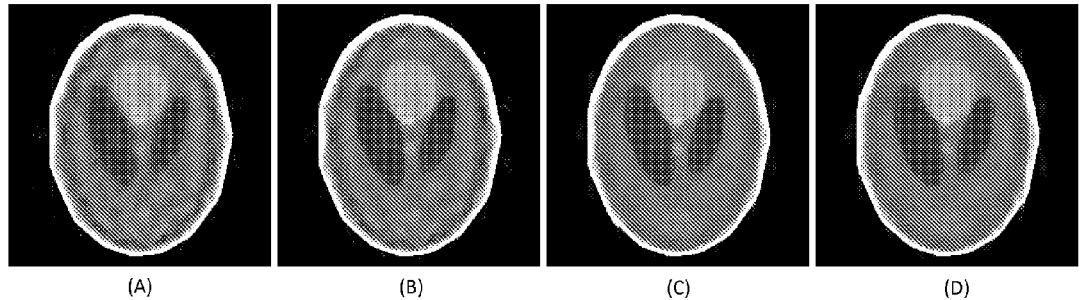
FIG. 13 are reconstructions from 15 noise-free projections. (A)-(D) are counterparts of that in FIG. 12.

To demonstrate the validity of the proposed algorithms, we implemented them in MatLab and performed numerical tests. We assumed a circular scanning locus of radius 57.0 cm and fan-beam geometry. The object was a modified Shepp-Logan phantom in a compact support with a radius of 10.0 cm. We used an equi-distance virtual detector array of length 20.0 cm. The detector was centered at the system origin and made perpendicular to the direction from the origin to the x-ray source. The detector array consisted of 256 elements. For each of our selected numbers of projections over a full-scan range, we first equi-angularly acquired the corresponding projection dataset based on the discrete projection model shown in FIG. 8. Then, we reconstructed the images using the following four methods: (1) the classical SART iteration method without the regularization of sparsity, (2) the TV minimization algorithm using the steepest descent search method, (3) the TV minimization algorithm with soft-threshold filtering, and (4) the TD minimization method with soft-threshold filtering. For all the above methods, the stopping criterion was defined as reaching the maximum iteration number 2,000. The threshold w for the third and fourth algorithms was set 0.004. FIGS. 12 and 13 show the reconstructed 256×256 images from 21 and 15 projections, respectively. In general, the proposed algorithms perform much better than the available steepest descent algorithm.

II.4. Interior Reconstruction from Coded-Aperture-Generated Projections

In recent years, coded aperture is a new technology to improve image quality and reduce radiation dose. Using the multi-source and coded aperture technology, we can obtain a compressive sampling based imaging system with an optimized sampling pattern allowing flexibility of source-multiplexing, projection modulation and overlapping. To reconstruct an image from aperture coded projections, we must solve the reconstruction problem from coded projections. There are numerous cases in this category.

For example, we developed a POCS-based algorithm to solve the so-called overlapping problem (G. Wang, L. Yang, Y. Lu: Method for Image Reconstruction from Overlapped Projections, VTIP No.: 10-058, Dec. 2, 2009; L. Yang, Y. Lu, and G. Wang, *Compressed sensing based image reconstruction from overlapped projections*, International Journal of Biomedical Imaging, to appear).

As another example, we developed a SART-based formula for this problem. Let $f=[f_1, f_2, \ldots, f_N]^T \in \mathbb{R}^N$ be an object function and $g=[g_1, g_2, \ldots, g_M]^T \in \mathbb{R}^M$ be a set of measurements. Usually, for the two-source case, they are linked by:

$$g = e^{-A_1 f} + e^{-A_2 f}, \quad (II.37)$$

where $A_1=(a_{mn}) \in \mathbb{R}^M \times \mathbb{R}^N$ and $A_2=(a_{mn}) \in \mathbb{R}^M \times \mathbb{R}^N$ are the linear measurement matrix. Assume that the current estimation of the image is $f^k$, we have an error image $\Delta f^k = f - f^k$ and hence $$g = e^{-A_1(f^k + \Delta f^k)} + e^{-A_2(f^k + \Delta f^k)} \quad (II.38)$$
$$= e^{-A_1 f^k} e^{-A_1 \Delta f^k} + e^{-A_2 f^k} e^{-A_2 \Delta f^k}$$
$$\approx e^{-A_1 f^k}(1 - A_1 \Delta f^k) + e^{-A_2 f^k}(1 - A_2 \Delta f^k),$$

where the 1$^{st}$ order Taylor expansion has been used. Eq. (II.38) implied that $$e^{-A_1 f^k} + e^{-A_2 f^k} - g = (e^{-A_1 f^k} A_1 + e^{-A_2 f^k} A_2) \Delta f^k. \quad (II.39)$$

Consider $(e^{-A_1 f^k} + e^{-A_2 f^k} - g)$ as the measurement data and $(e^{-A_1 f^k} A_1 + e^{-A_2 f^k} A_2)$ as the measurement matrix, we can use our SART-type algorithm (Eq. II.16) to solve $\Delta f^k$. However, it is not necessary to obtain an exact solution for $\Delta f^k$. Instead, we only need one step iteration to estimate $\Delta f^k$, then update the current image by $f^{k+1} = f^k + \Delta f^k$. This algorithm is convergent and stable. And it can be used for both global and interior reconstruction. The algorithm for the overlapped projections can be summarized as:

> S1. Initialize $\alpha$, $f^{(0)}$ and k;
> S2. Estimate R(f*, p);
> S3. Update the current estimation iteratively:
> S3.1. k := k + 1;
> S3.2. Compute $A = e^{-A_1 f^k} A_1 + e^{-A_2 f^k} A_2$ and $\tilde{g} = e^{-A_1 f^k} + e^{-A_2 f^k} - g$;
> S3.3. Compute $a_{+n}$ and $a_{m+}$;
> S3.4. Estimate $\Delta f^k$ by the formula $\Delta f^k := \Lambda^{+N} A^T \Lambda^{M+} \tilde{g}$;

-continued

S.3.5. $\tilde{f}^k := f^{k-1} + \alpha \Delta \tilde{f}^k$;
S.3.6. Compute the sparse transform $\phi_\gamma := \langle \tilde{f}^k, \varphi_\gamma \rangle$ for $\gamma \in \Gamma$;
S.3.7. Estimate the adapted threshold $\mu$;
S.3.8. Perform the soft-thresholding $\tilde{\phi}_\gamma := S_{\mu,p}(\phi_\gamma)$;

S.3.9. Perform the inverse sparse transform $f^k := \sum_{\gamma \in \Gamma} \tilde{\phi}_\gamma \varphi_\gamma$;

S.4. Go to S.3 until certain the convergence criteria are satisfied.

Figure 14:
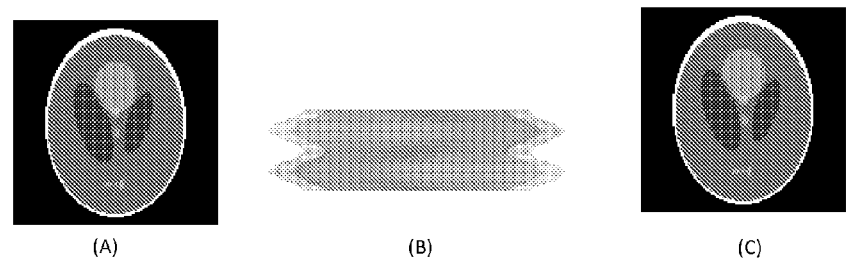
FIG. 14 is the reconstructions from 51 noise-free and overlapped projections. (A) The original phantom image, (B) the overlapped projections, and (C) reconstructed result by TD minimization. The display window for (A) and (C) is [0,0.5].

The above algorithm was implemented in Matlab and tested by a numerical phantom. In our numerical simulation, we assumed two x-ray sources and one shared equi-distant detector. Totally, 51 projections were acquired in a full scan range, and the TD sparsity was employed. As shown in FIG. 14, our results are excellent.

Figure 15:
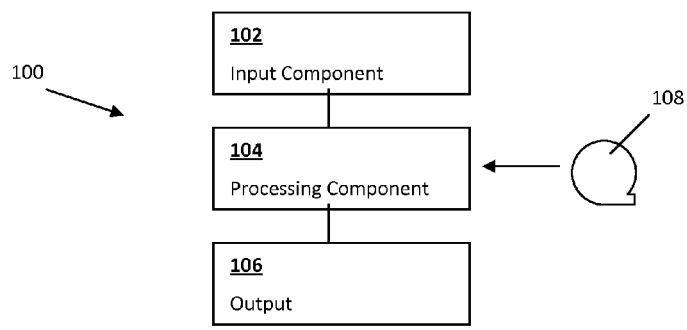
FIG. 15 is a schematic diagram of an example of hardware on which the preferred or other embodiments can be implemented.

FIG. 15 is a schematic diagram of an example of hardware 100 on which the preferred or other embodiments can be implemented. The imaging component 102 can be any imaging component capable of operating as described above, any equivalent thereof, or any device for receiving imaging data remotely or from storage. The processing component 104 can be any processor capable of performing the operations disclosed above or any equivalents thereof. The output 106 can include one or more of a display, persistent storage, a printer, a communication facility for transmitting the results remotely, or any other form of output. The software for performing the operations disclosed above can be supplied on any form of persistent storage 108 or in any other manner, e.g., over a network connection.

While a preferred embodiment has been set forth above, those skilled in the art who have reviewed the present disclosure will readily appreciate that other embodiments can be realized within the scope of the invention. For example, numerical values are illustrative rather than limiting, as are recitations of particular software. Therefore, the present invention should be construed as limited only by the appended claims.

What is claimed is:

1. A method for compressed sensing based interior tomography, the method comprising:
    (a) obtaining a truncated local projection dataset through an interior scan that directly involves a region-of-interest (ROI) or volume-of-interest (VOI) inside an object to be reconstructed;
    (b) reconstructing, in a computing device, the ROI/VOI by minimizing a weighted sum of (i) a function of an Lp ($0 \le p \le 2$) image norm of a sparsifying transform of the object to be reconstructed, and (ii) a $L_2$ norm of a difference between measured and the forward projection datasets of the object to be reconstructed, or an $L_2$ norm of a difference between a backprojected image of differential projection data and a Hilbert transform image of the object to be reconstructed, regularizing by other available knowledge selected from the group consisting of bounds of image intensities, compact support of the object, scout views, direct current component of the object, and texture features; and
    (c) outputting the reconstructed ROI/VOI.

2. The method of claim 1, wherein the image norm function is an Lp norm with $0 \le p \le 2$, or a mixed norm with at least two values of p.

3. The method of claim 1, wherein the dataset is measured using an x-ray imaging system or in another straight or approximately straight ray imaging geometry.

4. The method of claim 1, wherein the projection dataset is measured in terms of functions of weighted sums of unknowns along a bundle of paths that are close to each other.

5. The method of claim 3, wherein the imaging system uses a single or multi-sources.

6. The method of claim 5, wherein multi-sources are modulated by coded apertures, share one or more detectors, and are fired simultaneously or sequentially.

7. The method of claim 1, wherein the minimization is with respect to an Lp norm with $0 \le p \le 2$, or a mixed norm with at least two values of p.

8. The method of claim 1, wherein the said sparsifying transform is an invertible transform or frame.

9. The method of claim 8, wherein the invertible transform or frame is a wavelet transform, Fourier transform, or another lossless image compressive transform or encoding method.

10. The method of claim 1, wherein the said sparsifying transform is an un-invertible transform.

11. The method of claim 10, wherein the un-invertible transform is a discrete gradient transform, discrete difference transform, or high-order transform.

12. The method of claim 1, wherein step (a) includes global projection measurements in terms of two or more scout views.

13. The method of claim 1, wherein step (b) comprises:
    (i) minimizing a data discrepancy defined as the $L_2$ norm of the difference between the measured and forward projection datasets of the object to be reconstructed, or the $L_2$ norm of the difference between the backprojected image of the differential projection data and the Hilbert transform image of the object to be reconstructed; and
    (ii) minimizing an image norm function defined as a function of an Lp ($0 \le p \le 2$) norm of a sparsifying transform of the object to be reconstructed;
    wherein steps (i) and (ii) are iteratively performed in an alternating manner.

14. The method of claim 13, wherein step (i) is implemented in an OS-SART framework.

15. The method of claim 13, wherein step (i) is implemented in a statistical framework such as using a maximum likelihood (ML) transmission CT approach.

16. The method of claim 15, wherein the statistical framework is a maximum-likelihood (ML) reconstruction with a signal sparsity model based constraint or penalty.

17. The method of claim 16, wherein the signal sparsity model based constraint is a total variation.

18. The method of claim 13, where in step (ii) is implemented using a steepest decent search method.

19. The method of claim 13, wherein step (ii) is implemented by a soft-threshold filtering method.

20. The method of claim 19, wherein the soft threshold filtering method comprises:
    (i) computing a sparse transform;
    (ii) estimating an adapted threshold;
    (iii) performing soft-threshold filtering with respect to a kernel function $$S_{w,1}(x) = \begin{cases} x - w & \text{if } x \ge w \\ 0 & \text{if } |x| < w \\ x + w & \text{if } x \le -w \end{cases},$$

where w is a threshold value, w is an input and $S_{w,1}(x)$ is the output; and
    (iv) performing an inverse sparse transform.

21. The method of claim 20, wherein the inverse transform of a discrete gradient transform is constructed as $$f_{i,j}^k = \lambda_a f_{i,j}^{k,a} + \lambda_b f_{i,j}^{k,b} + \lambda_c f_{i,j}^{k,c},$$

$$f_{i,j}^{k,a} = \begin{cases} \dfrac{2\tilde{f}_{i,j}^k + \tilde{f}_{i+1,j}^k + \tilde{f}_{i,j+1}^k}{4}, & \text{if } d_{i,j}^k < w \\ \tilde{f}_{i,j}^k - \dfrac{w(2\tilde{f}_{i,j}^k - \tilde{f}_{i+1,j}^k - \tilde{f}_{i,j+1}^k)}{4 d_{i,j}^k}, & \text{if } d_{i,j}^k \geq w, \end{cases}$$

$$f_{i,j}^{k,b} = \begin{cases} \dfrac{\tilde{f}_{i,j}^k + \tilde{f}_{i-1,j}^k}{2}, & \text{if } d_{i-1,j}^k < w \\ \tilde{f}_{i,j}^k - \dfrac{w(\tilde{f}_{i,j}^k - \tilde{f}_{i-1,j}^k)}{2 d_{i-1,j}^k}, & \text{if } d_{i-1,j}^k \geq w, \end{cases}$$

$$f_{i,j}^{k,c} = \begin{cases} \dfrac{\tilde{f}_{i,j}^k + \tilde{f}_{i,j-1}^k}{2}, & \text{if } d_{i,j-1}^k < w \\ \tilde{f}_{i,j}^k - \dfrac{w(\tilde{f}_{i,j}^k - \tilde{f}_{i,j-1}^k)}{2 d_{i,j-1}^k}, & \text{if } d_{i,j-1}^k \geq w; \end{cases}$$

where $\lambda_a + \lambda_b + \lambda_c = 1$.

22. The method of claim 20, wherein the inverse transform of a discrete gradient transform is any non-linear filter for the reconstructed image to achieve the goal of soft-threshold filtering with respect to a given threshold.

23. The method of claim 20, wherein the inverse transform of a discrete difference transform is constructed as $$f_{i,j}^k = \lambda_a q(w, \tilde{f}_{i,j}^k, \tilde{f}_{i+1,j}^k) + \lambda_b q(w, \tilde{f}_{i,j}^k, \tilde{f}_{i,j+1}^k) + \lambda_c q(w, \tilde{f}_{i,j}^k, \tilde{f}_{i,j-1}^k) + \lambda_d q(w, \tilde{f}_{i,j}^k, \tilde{f}_{i-1,j}^k),$$

$$q(w, y, z) = \begin{cases} \dfrac{y+z}{2}, & \text{if } |y-z| < w \\ y - \dfrac{w}{2}, & \text{if } (y-z) \geq w \\ y + \dfrac{w}{2}, & \text{if } (y-z) \leq -w; \end{cases}$$

where $\lambda_a + \lambda_b + \lambda_c + \lambda_d = 1$.

24. The method of claim 20, wherein the inverse transform of a discrete difference transform is a non-linear filter for the reconstructed image to achieve the goal of soft-threshold filtering with respect to a given threshold.

25. The method of claim 20, wherein the inverse transform of a un-invertible sparsifying transform is constructed as a non-linear filter for the reconstructed image to achieve the goal of soft-threshold filtering with respect to a given threshold.

26. A system for compressed sensing based interior tomography, the system comprising:
(a) an imaging component for obtaining a truncated local projection dataset through an interior scan that directly involves a region-of-interest (ROI) or volume-of-interest (VOI) inside an object to be reconstructed;
(b) a processing component for reconstructing the ROI/VOI by minimizing a weighted sum of (i) a function of an Lp ($0 \leq p \leq 2$) image norm of a sparsifying transform of an object to be reconstructed, and (ii) an $L_2$ norm of a difference between the measured and forward projection datasets of the reconstructed, or an $L_2$ norm of a difference between a backprojected image of the differential projection data and a Hilbert transform image of the object to be reconstructed, regularized by other available knowledge selected from the group consisting of bounds of image intensities, compact support of the object, scout views, direct current component of the object; and
(c) an output, in communication with a processing component, for outputting the reconstructed ROI/VOI.

27. The system of claim 26, wherein the image norm function is an ln norm with $0 \leq p \leq 2$, or a mixed norm with at least two p values.

28. The system of claim 26, wherein the imaging component comprises an x-ray imaging system or another straight or approximately straight ray imaging geometry.

29. The system of claim 26, wherein the dataset is measured in terms of functions of weighted sums of unknowns along a bundle of paths that are close to each other.

30. The system of claim 28, wherein the imaging component uses a single or multi-sources.

31. The system of claim 30, wherein multi-sources are modulated by coded apertures, share one or more detectors, and are fired simultaneously or sequentially.

32. The system of claim 26, wherein the minimization is with respect to an Lp norm with $0 \leq p \leq 2$, or a mixed norm with at least two p values.

33. The system of claim 26, wherein the said sparsifying transform is an invertible transform or frame.

34. The system of claim 33, wherein the invertible transform or frame is a wavelet transform, Fourier transform, or another lossless image compressive transform or encoding method.

35. The system of claim 26, wherein the said sparsifying transform is an un-invertible transform.

36. The system of claim 35, wherein the un-invertible transform is a discrete gradient transform, discrete difference transform, or high-order transform.

37. The system of claim 26, wherein the imaging component takes global projection measurements in terms of two or more scout views.

38. The system of claim 26, wherein the processing component performs:
(i) minimizing, a data discrepancy defined as the $L_2$ norm of the difference between the measured and the forward projection datasets of the object to be reconstructed, or the $L_2$ norm of the difference between the backprojected image of the differential projection data and the Hilbert transform image of the object to be reconstructed; and
(ii) minimizing an image norm function defined as a function of an Lp ($0 \leq p \leq 2$) image norm of a sparsifying transform of the object to be reconstructed;
wherein the processing component performs steps (i) and (ii) iteratively in an alternating manner.

39. The system of claim 38, wherein the imaging component implements an OS-SART framework.

40. The system of claim 38, wherein step (i) is implemented in a statistical framework such as using a maximum likelihood (ML) transmission CT approach.

41. The system of claim 40, wherein the statistical framework is a maximum-likelihood (ML) reconstruction with a signal sparsity model based constraint or penalty.

42. The system of claim 41, wherein the signal sparsity model based constraint is a total variation.

43. The system of claim 38, wherein the processing component performs a steepest decent search method.

44. The system of claim 38, wherein the processing component performs a soft-threshold filtering method.

45. The system of claim 44, wherein the soft threshold filtering method comprises:
(i) computing a sparse transform;
(ii) estimating an adapted threshold;

(iii) performing soft-threshold filtering with respect to a kernel function $$S_{w,1}(x) = \begin{cases} x - w & \text{if } x \geq w \\ 0 & \text{if } |x| < w \\ x + w & \text{if } x \leq -w \end{cases}$$

where w is a threshold value, w is an input and $S_{w,1}(x)$ is the output; and (iv) performing an inverse sparse transform.

46. The system of claim 45, wherein the inverse transform of a discrete gradient transform is constructed as $$f_{i,j}^k = \lambda_a f_{i,j}^{k,a} + \lambda_b f_{i,j}^{k,b} + \lambda_c f_{i,j}^{k,c},$$

$$f_{i,j}^{k,a} = \begin{cases} \dfrac{2\tilde{f}_{i,j}^k + \tilde{f}_{i+1,j}^k + \tilde{f}_{i,j+1}^k}{4}, & \text{if } d_{i,j}^k < w \\ \tilde{f}_{i,j}^k - \dfrac{w(2\tilde{f}_{i,j}^k - \tilde{f}_{i+1,j}^k - \tilde{f}_{i,j+1}^k)}{4d_{i,j}^k}, & \text{if } d_{i,j}^k \geq w, \end{cases}$$

$$f_{i,j}^{k,b} = \begin{cases} \dfrac{\tilde{f}_{i,j}^k + \tilde{f}_{i-1,j}^k}{2}, & \text{if } d_{i-1,j}^k < w \\ \tilde{f}_{i,j}^k - \dfrac{w(\tilde{f}_{i,j}^k - \tilde{f}_{i-1,j}^k)}{2d_{i-1,j}^k}, & \text{if } d_{i-1,j}^k \geq w, \end{cases}$$

$$f_{i,j}^{k,c} = \begin{cases} \dfrac{\tilde{f}_{i,j}^k + \tilde{f}_{i,j-1}^k}{2}, & \text{if } d_{i,j-1}^k < w \\ \tilde{f}_{i,j}^k - \dfrac{w(\tilde{f}_{i,j}^k - \tilde{f}_{i,j-1}^k)}{2d_{i,j-1}^k}, & \text{if } d_{i,j-1}^k \geq w; \end{cases}$$

where $\lambda_a + \lambda_b + \lambda_c = 1$.

47. The system of claim 45, wherein the inverse transform of a discrete gradient transform is any non-linear filter for the reconstructed image to achieve the goal of soft-threshold filtering with respect to a given threshold.

48. The system of claim 45, wherein the inverse transform of a discrete difference transform is constructed as $$f_{i,j}^k = \lambda_a q(w, \tilde{f}_{i,j}^k, \tilde{f}_{i+1,j}^k) + \lambda_b q(w, \tilde{f}_{i,j}^k, \tilde{f}_{i,j+1}^k) + \lambda_c q(w, \tilde{f}_{i,j}^k, \tilde{f}_{i,j-1}^k) + \lambda_d q(w, \tilde{f}_{i,j}^k, \tilde{f}_{i-1,j}^k),$$

$$q(w, y, z) = \begin{cases} \dfrac{y+z}{2}, & \text{if } |y - z| < w \\ y - \dfrac{w}{2}, & \text{if } (y - z) \geq w \\ y + \dfrac{w}{2}, & \text{if } (y - z) \leq -w; \end{cases}$$

where $\lambda_a + \lambda_b + \lambda_c + \lambda_d = 1$.

49. The system of claim 45, wherein the inverse transform of a discrete difference transform is a non-linear filter for the reconstructed image to achieve the goal of soft-threshold filtering with respect to a given threshold.

50. The system of claim 45, wherein the inverse transform of a un-invertible sparsifying transform is constructed as a non-linear filter for the reconstructed image to achieve the goal of soft-threshold filtering with respect to a given threshold.

* * * * *

UNITED STATES PATENT AND TRADEMARK OFFICE
CERTIFICATE OF CORRECTION

PATENT NO. : 8,811,700 B2
APPLICATION NO. : 13/264834
DATED : August 19, 2014
INVENTOR(S) : Ge Wang et al.

Page 1 of 1

It is certified that error appears in the above-identified patent and that said Letters Patent is hereby corrected as shown below:

In the specification

Column 1 lines 6-9 should read as follows

This invention was made with government support under Grant Nos. EB002667 and EB004287 awarded by the National Institutes of Health. The government has certain rights in the invention.

Signed and Sealed this
Fifth Day of April, 2016

Michelle K. Lee
*Director of the United States Patent and Trademark Office*